United States Patent [19]
Sledziewski et al.

[11] Patent Number: 5,576,210
[45] Date of Patent: Nov. 19, 1996

[54] MAMMALIAN/YEAST HYBRID G PROTEIN-COUPLED RECEPTORS

[75] Inventors: Andrzej Z. Sledziewski, Seattle; Paul O. Sheppard, Redmond, both of Wash.

[73] Assignee: ZymoGenetics, Inc., Seattle, Wash.

[21] Appl. No.: 192,634

[22] Filed: Feb. 7, 1994

Related U.S. Application Data

[62] Division of Ser. No. 478,100, Feb. 8, 1990, Pat. No. 5,284,746.

[51] Int. Cl.$^6$ .............................. C12N 1/19; C12N 15/62
[52] U.S. Cl. ..................... 435/254.21; 435/64.7; 435/252.3; 435/320.1; 536/23.4
[58] Field of Search .................... 435/64.7, 6, 252.3, 435/320.1, 255; 536/23.4

[56] References Cited

U.S. PATENT DOCUMENTS

| | | | |
|---|---|---|---|
| 4,745,057 | 5/1988 | Beckage et al. | 435/68 |
| 4,859,609 | 8/1989 | Dull et al. | 436/501 |
| 4,931,373 | 6/1990 | Kawasaki et al. | 435/69.2 |
| 5,037,743 | 8/1991 | Welch et al. | 435/69.1 |

FOREIGN PATENT DOCUMENTS

| | | |
|---|---|---|
| 244221 | 11/1987 | European Pat. Off. . |
| 351921 | 1/1990 | European Pat. Off. . |

OTHER PUBLICATIONS

Science vol. 240: 1310–1346, 03 Jun. 1988, Kobska et al.
Feb. 241 (1,2): 119–125, Dec. 1988 Kwbo et al.
Cell 55:221–234, 21 Oct. 1988, Reneke et al.
Lefkowitz et al., "Adenylate Cyclase–Coupled Beta–Adrenergic Receptors: Structure and Mechanisms of Activation and Desensitization", *Ann. Rev. Biochem.* 52: 159–186, 1983.
Marullo et al., "Expression of Human β1 and β2 Adrenergic Receptors in *E. Coli* and a New Tool for Ligand Screening", *Bio/Technology* 7:923–927, 1989.
Yarden et al., "The Avian β–Adrenergic Receptor: Primary Structure and Membrane Topology", *Proc. Natl. Acad. Sci. USA* 83: 6795–6799, 1986.
Minneman et al., "A Comparison of the Beta –Adrenergic Receptor of the Turkey Erythrocyte with Mammalian Beta $_1$ and Beta $_2$ Receptors", *Mol. Pharmacol.* 17: 1–7, 1980.
Dixon et al., "Cloning of the Gene and cDNA for Mammalian β–Adrenergic Receptor and Homology with Rhodopsin", *Nature* 321: 75–79, 1986.
Kobilka et al., "cDNA for the Human β $_2$–Adrenergic Receptor: A Protein with Multiple Membrane–Spanning Domains and Encoded by a Gene Whose Chromosomal Location is Shared with that of the Receptor for Platelet–Derived Growth Factor", *Proc. Natl. Acad. Sci. USA* 84: 46–50, 1987.
Emorine et al., "Structure of the Gene for Human β $_2$Adrenergic Receptor: Expression and Promoter Characterization", *Proc. Natl. Acad. Sci. USA* 84: 6995–6999, 1987.

Stiles, "Deglycosylated Mammalian β$_2$–Adrenergic Receptors: Effect on Radioligand Binding and Peptide Mapping", *Arch. Biiochem. Biophys.* 237: 65–71, 1985.
Nathans and Hogness, "Isolation, Sequence Analysis, and Intron–Exon Arrangement of the Gene Encoding Bovine Rhodopsin" *Cell* 34: 807–814, 1983.
Kobilka et al., "Cloning, Sequencing, and Expression of the Gene Coding for the Human Platelet α$_2$–Adrenergic Receptor", *Science* 238: 650–656, 1987.
Young et al., "Isolation and Characterization of a New Cellular Oncogene Encoding a Protein with Multiple Potential Transmembrane Domains", *Cell* 45: 711–719, 1986.
Jackson et al., "The Mas Oncogene Encodes an Angiotensin Receptor", *Nature* 335: 437–439, 1988.
Masu et al., "cDNA Cloning of Bovine Substance–K Receptor Through Oocyte Expression System", *Nature* 329: 836–838, 1987.
Kubo et al., "Cloning, Sequencing and Expression of Complementary DNA Encoding the Muscarinic Acetylcholine Receptor", *Nature* 323: 411–416, 1986.
Panayotou and Waterfield, "Cell Surface Receptors for Polypeptide Hormones, Growth Factors and Neuropeptides" *Curr Opinion Cell Biol.* 1: 167–176, 1989.
Kyte and Doolittle, "A Simple Method for Displaying the Hydropathic Character of a Protein", *J. Mol. Biol.* 157: 105–132, 1982.
Dixon et al., "Ligand Binding to the β–Adrenergic Receptor Involves its Rhodopsin–Like Core", *Nature* 326: 73–77, 1987.
Strader et al., "Conserved Aspartic Acid Residues 79 and 113 of the β–Adrenergic Receptor Have Different Roles in Receptor Function", *J. Biol. Chem.* 263: 10267–10271, 1988.
Strader et al., "Identification of Two Serine Residues Involved in Agonist Activation of the β–Adrenergic Receptor", *J. Biol. Chem.* 264: 13572–13578, 1989.
Nakayama et al., "Nucleotide Sequences of STE2 and STE3, Cell Type–Specific Sterile Genes from *Saccharomyces cerevisiae*", *EMBO J.* 4: 2643–2648, 1985.

(List continued on next page.)

*Primary Examiner*—John Ulm
*Attorney, Agent, or Firm*—Gary E. Parker; Debra K. Leith; Deborah A. Sawislak

[57] ABSTRACT

Methods are disclosed for producing hybrid G protein-coupled receptors. DNA sequences encoding hybrid G protein-coupled receptors are provided, wherein the receptors comprise mammalian G protein-coupled receptors having at least one domain other than the ligand-binding domain replaced with a corresponding domain of a yeast G protein-coupled receptor. DNA constructs comprising the following operatively linked elements: a transcriptional promoter, a DNA sequence encoding a hybrid G protein-coupled receptor, wherein the receptor comprises a mammalian G protein-coupled receptor having at least one domain other than the ligand-binding domain replaced with a corresponding domain of a yeast G protein-coupled receptor, and a transcriptional terminator. Host cells transformed with the DNA constructs and methods utilizing the transformed cells are also provided.

18 Claims, 20 Drawing Sheets

OTHER PUBLICATIONS

Burkholder and Hartwell, "The Yeast α–Factor Receptor: Structural Properties Deduced from the Sequence of the STE2 Gene", *Nuc. Acids Res.* 13: 8463–8475, 1985.

Marsh and Herskowitz, "STE2 Protein of *Saccharomyces kluyveri* is a Member of the Rhodopsin/β–Adrenergic Receptor Family and is Responsible for Recognition of the Peptide Ligand α Factor", *Proc. Natl. Acad. Sci. USA* 85: 3855–3859, 1988.

Hagen et al., "Evidence the Yeast STE3 Gene Encodes a Receptor for the Peptide Pheromone a Factor: Gene Sequence and Implications for the Structure of the Presumed Receptor", *Proc. Natl. Acad. Sci. USA* 83: 1418–1422, 1986.

Frielle et al., "Cloning of the cDNA for the Human $\beta_1$–Adrenergic Receptor", *Proc. Natl. Acad. Sci. USA* 84: 7920–7924, 1987.

Dohlman et al., "A Family of Receptors Coupled to Guanine Nucleotide Regulatory Proteins", *Biochemistry* 26: 2657–2664, 1987.

Herskowitz and Marsh, "Conservation of a Receptor/Signal Transduction System", *Cell* 50: 995–996, 1987.

Kronstad et al., "A Yeast Operator Overlaps an Upstream Activation Site", *Cell* 59: 369–377, 1986.

MacKay et al., "The *Saccharomyces cerevisiae* BAR1 Gene Encodes an Exported Protein with Homology to Pepsin", *Proc. Natl. Acad. Sci. USA* 85:55–59, 1988.

Miller, "Assay of β–Galactosidase", Experiments in Molecular Genetics pp. 352–355 (Cold Spring Harbor, 1972).

Rothstein, "One–Step Gene Disruption in Yeast", *Meth. Enzymol.* 101:202–211, 1983.

Cotecchia et al., "Molecular Cloning and Expression of the cDNA for the Hamster $a_1$–Argenergic. Receptor", *Proc. Natl. Acad. Sci. USA* 85:7159–7163, 1988.

McCaffrey et al., "Identification and Regulation of a Gene Required for Cell Fusion During Mating of Yeast *Saccharomyces cerevisiae*", *Mol. and Cell. Biol.* 7:2680–2690, 1987.

Marullo et al., "Human $\beta_2$–Adrenergic Receptors Expressed in *Escherichia coli* Membranes Retain Their Pharmacological Properties", *Proc. Natl. Acad. Sci. USA* 85:7551–7555, 1988.

Lefkowitz and Caron, "Adrenergic Receptors", *J. Biol. Chem.* 263:4993–4996, 1988.

Trueheart et al., "Two Genes Required for Cell Fusion During Yeast Conjugation: Evidence for a Pheromone–Induced Surface Protein", *Mol. and Cell. Biol.* 7:2316–2328, 1987.

FIG. 3A

```
                              30
ATG GGG CCA CCC GGG AAC GAC AGT GAC TTC TTG CTG ACA ACC AAC GGA
Met Gly Pro Pro Gly Asn Asp Ser Asp Phe Leu Leu Thr Thr Asn Gly 60                                      90
AGC CAT GTG CCA GAC CAC GAT GTC ACT GAG GAA CGG GAC GAA GCA TGG
Ser His Val Pro Asp His Asp Val Thr Glu Glu Arg Asp Glu Ala Trp

120
GTG GTA GGC GCC ATC CTT ATG TCG GTT ATC GTC CTG GCC ATC GTG TTT
Val Val Gly Ala Ile Leu Met Ser Val Ile Val Leu Ala Ile Val Phe 150                                     180
GGC AAC GTG CTG GTC ATC ACA GCC ATT GCC AAG TTC GAG AGG CTA CAG
Gly Asn Val Leu Val Ile Thr Ala Ile Ala Lys Phe Glu Arg Leu Gln 210                                     240
ACT GTC ACC AAC TAC TTC ATA ACC TCC TTG GCG TGT GCT GAT CTA GTC
Thr Val Thr Asn Tyr Phe Ile Thr Ser Leu Ala Cys Ala Asp Leu Val

270
ATG GGC CTA GCG GTG GTG CCG TTT GGG GCC AGT CAC ATC CTT ATG AAA
Met Gly Leu Ala Val Val Pro Phe Gly Ala Ser His Ile Leu Met Lys
                                                  L2

300                                       330
ATG TGG AAT TTT GGC AAC TTC TGG TGC GAG TTC TGG ACT TCC ATT GAT
Met Trp Asn Phe Gly Asn Phe Trp Cys Glu Phe Trp Thr Ser Ile Asp

360
GTG TTA TGC GTC ACA GCC AGC ATT GAG ACC CTG TGC GTG ATA GCA GTG
Val Leu Cys Val Thr Ala Ser Ile Glu Thr Leu Cys Val Ile Ala Val 390                                     420
GAT CGC TAC ATT GCT ATC ACA TCG CCA TTC AAG TAC CAG AGC CTG CTG
Asp Arg Tyr Ile Ala Ile Thr Ser Pro Phe Lys Tyr Gln Ser Leu Leu
```

FIG. 3B

```
                450                                                          480
ACC AAG AAT AAG GCC CGA ATG GTC ATC CTA ATG GTG TGG ATT GTA TCC
Thr Lys Asn Lys Ala Arg Met Val Ile Leu Met Val Trp Ile Val Ser

510
GGC CTT ACC TCC TTC TTG CCC ATT CAG ATG CAC TGG TAC CGT GCC ACC
Gly Leu Thr Ser Phe Leu Pro Ile Gln Met His Trp Tyr Arg Ala Thr
                                         L4

540                                        570
CAC CAG AAA GCC ATC GAC TGC TAT CAC AAG GAG ACT TGC TGC GAC TTC
His Gln Lys Ala Ile Asp Cys Tyr His Lys Glu Thr Cys Cys Asp Phe

600
TTC ACG AAC CAG GCC TAC GCC ATT GCT TCC TCC ATT GTA TCT TTC TAC
Phe Thr Asn Gln Ala Tyr Ala Ile Ala Ser Ser Ile Val Ser Phe Tyr 630                                          660
GTG CCT CTA GTG GTC ATG GTC TTT GTC TAT TCC AGG GTC TTC CAG GTG
Val Pro Leu Val Val Met Val Phe Val Tyr Ser Arg Val Phe Gln Val 690                                      720
GCC AAA AGG CAG CTC CAG AAG ATA GAC AAA TCT GAG GGA AGA TTC CAC
Ala Lys Arg Gln Leu Gln Lys Ile Asp Lys Ser Glu Gly Arg Phe His

750
TCC CCA AAC CTC GGC CAG GTG GAG CAG GAT GGG CGG AGT GGG CAC GGA
Ser Pro Asn Leu Gly Gln Val Glu Gln Asp Gly Arg Ser Gly His Gly 780                                        810
CTC CGA AGG TCC TCC AAG TTC TGC TTG AAG GAG CAC AAA GCC CTC AAG
Leu Arg Arg Ser Ser Lys Phe Cys Leu Lys Glu His Lys Ala Leu Lys

840
ACT TTA GGC ATC ATC ATG GGC ACA TTC ACC CTC TGC TGG CTG CCC TTC
Thr Leu Gly Ile Ile Met Gly Thr Phe Thr Leu Cys Trp Leu Pro Phe
```

FIG. 3C

```
     870                                   900
TTC ATT GTC AAC ATC GTG CAC GTG ATC CAG GAC AAC CTC ATC CCT AAG
Phe Ile Val Asn Ile Val His Val Ile Gln Asp Asn Leu Ile Pro Lys 930                                   960
GAA GTT TAC ATC CTC CTT AAC TGG TTG GGC TAT GTC AAT TCT GCT TTC
Glu Val Tyr Ile Leu Leu Asn Trp Leu Gly Tyr Val Asn Ser Ala Phe

990
AAT CCC CTC ATC TAC TGT CGG AGT CCA GAT TTC AGG ATT GCC TTC CAG
Asn Pro Leu Ile Tyr Cys Arg Ser Pro Asp Phe Arg Ile Ala Phe Gln 1020                                  1050
GAG CTT CTA TGC CTC CGC AGG TCT TCT TCA AAA GCC TAT GGG AAC GGC
Glu Leu Leu Cys Leu Arg Arg Ser Ser Ser Lys Ala Tyr Gly Asn Gly

1080
TAC TCC AGC AAC AGT AAT GGC AAA ACA GAC TAC ATG GGG GAG GCG AGT
Tyr Ser Ser Asn Ser Asn Gly Lys Thr Asp Tyr Met Gly Glu Ala Ser 1110                                   1140
GGA TGT CAG CTG GGG CAG GAA AAA GAA AGT GAA CGG CTG TGT GAG GAC
Gly Cys Gln Leu Gly Gln Glu Lys Glu Ser Glu Arg Leu Cys Glu Asp 1170                                  1200
CCC CCA GGC ACG GAA AGC TTT GTG AAC TGT CAA GGT ACT GTG CCT AGC
Pro Pro Gly Thr Glu Ser Phe Val Asn Cys Gln Gly Thr Val Pro Ser

1230
CTT AGC CTT GAT TCC CAA GGG AGG AAC TGT AGT ACA AAT GAC TCA CCG
Leu Ser Leu Asp Ser Gln Gly Arg Asn Cys Ser Thr Asn Asp Ser Pro

CTG TAA
Leu
```

FIG. 7A

```
                                    30                           15
ATG GGG CAA CCC GGG AAC GGC AGC GCC TTC TTG CTG GCA CCC AAT AGA
Met Gly Gln Pro Gly Asn Gly Ser Ala Phe Leu Leu Ala Pro Asn Arg 60                                        90
AGC CAT GCG CCG GAC CAC GAC GTC ACG CAG CAA AGG GAC GAG GTG TGG
Ser His Ala Pro Asp His Asp Val Thr Gln Gln Arg Asp Glu Val Trp
                                            TMD1
                        120
GTG GTG GGC ATG GGC ATC GTC ATG TCT CTC ATC GTC CTG GCC ATC GTG
Val Val Gly Met Gly Ile Val Met Ser Leu Ile Val Leu Ala Ile Val 150                                    180
TTT GGC AAT GTG CTG GTC ATC ACA GCC ATT GCC AAG TTC GAG CGT CTG
Phe Gly Asn Val Leu Val Ile Thr Ala Ile Ala Lys Phe Glu Arg Leu
                                                         TMD2
                   210                              240
CAG ACG GTC ACC AAC TAC TTC ATC ACT TCA CTG GCC TGT GCT GAT CTG
Gln Thr Val Thr Asn Tyr Phe Ile Thr Ser Leu Ala Cys Ala Asp Leu

270
GTC ATG GGC CTG GCA GTG GTG CCC TTT GGG GCC GCC CAT ATT CTT ATG
Val Met Gly Leu Ala Val Val Pro Phe Gly Ala Ala His Ile Leu Met
```

FIG. 7B

```
            300                                                  330
AAA ATG TGG ACT TTT GGC AAC TTC TGG TGC GAG TTT TGG ACT TCC ATT
Lys Met Trp Thr Phe Gly Asn Phe Trp Cys Glu Phe Trp Thr Ser Ile
                                    TMD3
                        360
GAT GTG CTG TGC GTC ACG GCC AGC ATT GAG ACC CTG TGC GTG ATC GCA
Asp Val Leu Cys Val Thr Ala Ser Ile Glu Thr Leu Cys Val Ile Ala 390                                         420
GTG GAT CGC TAC TTT GCC ATT ACT TCA CCT TTC AAG TAC CAG AGC CTG
Val Asp Arg Tyr Phe Ala Ile Thr Ser Pro Phe Lys Tyr Gln Ser Leu 450                                    480
CTG ACC AAG AAT AAG GCC CGG GTG ATC ATT CTG ATG GTG TGG ATT GTG
Leu Thr Lys Asn Lys Ala Arg Val Ile Ile Leu Met Val Trp Ile Val
                                              TMD4
                            510
TCA GGC CTT ACC TCC TTC TTG CCC ATT CAG ATG CAC TGG TAC CGG GCC
Ser Gly Leu Thr Ser Phe Leu Pro Ile Gln Met His Trp Tyr Arg Ala 540                                      570
ACC CAC CAG GAA GCC ATC AAC TGC TAT GCC AAT GAG ACC TGC TGT GAC
Thr His Gln Glu Ala Ile Asn Cys Tyr Ala Asn Glu Thr Cys Cys Asp
                                                         TMD5
                      600
TTC TTC ACG AAC CAA GCC TAT GCC ATT GCC TCT TCC ATC GTG TCC TTC
Phe Phe Thr Asn Gln Ala Tyr Ala Ile Ala Ser Ser Ile Val Ser Phe 630                                      660
TAC GTT CCC CTG GTG ATC ATG GTC TTC GTC TAC TCC AGG GTC TTT CAG
Tyr Val Pro Leu Val Ile Met Val Phe Val Tyr Ser Arg Val Phe Gln
```

FIG. 7C

```
                690                                              720
GAG GCC AAA AGG CAG CTC CAG AAG ATT GAC AAA TCT GAG GGC CGC TTC
Glu Ala Lys Arg Gln Leu Gln Lys Ile Asp Lys Ser Glu Gly Arg Phe

750
CAT GTC CAG AAC CTT AGC CAG GTG GAG CAG GAT GGG CGG ACG GGG CAT
His Val Gln Asn Leu Ser Gln Val Glu Gln Asp Gly Arg Thr Gly His 780                                    810
GGA CTC CGC AGA TCT TCC AAG TTC TGC TTG AAG GAG CAC AAA GCC CTC
Gly Leu Arg Arg Ser Ser Lys Phe Cys Leu Lys Glu His Lys Ala Leu
                                                        TMD6
                    840
AAG ACG TTA GGC ATC ATC ATG GGC ACT TTC ACC CTC TGC TGG CTG CCC
Lys Thr Leu Gly Ile Ile Met Gly Thr Phe Thr Leu Cys Trp Leu Pro 870                                 900
TTC TTC ATC GTT AAC ATT GTG CAT GTG ATC CAG GAT AAC CTC ATC CGT
Phe Phe Ile Val Asn Ile Val His Val Ile Gln Asp Asn Leu Ile Arg
                                                  TMD7
               930                                     960
AAG GAA GTT TAC ATC CTC CTA AAT TGG ATA GGC TAT GTC AAT TCT GGT
Lys Glu Val Tyr Ile Leu Leu Asn Trp Ile Gly Tyr Val Asn Ser Gly

990
TTC AAT CCC CTT ATC TAC TGC CGG AGC CCA GAT TTC AGG ATT GCC TTC
Phe Asn Pro Leu Ile Tyr Cys Arg Ser Pro Asp Phe Arg Ile Ala Phe 1020                                    1050
CAG GAG CTT CTG TGC CTG CGC AGG TCT TCT TTG AAG GCC TAT GGG AAT
Gln Glu Leu Leu Cys Leu Arg Arg Ser Ser Leu Lys Ala Tyr Gly Asn
```

FIG. 7D

```
                     1080
GGC TAC TCC AGC AAC GGC AAC ACA GGG GAG CAG AGT GGA TAT CAC GTG
Gly Tyr Ser Ser Asn Gly Asn Thr Gly Glu Gln Ser Gly Tyr His Val 1110                                1140
GAA CAG GAG AAA GAA AAT AAA CTG CTG TGT GAA GAC CTC CCA GGC ACG
Glu Gln Glu Lys Glu Asn Lys Leu Leu Cys Glu Asp Leu Pro Gly Thr 1170                                        1200
GAA GAC TTT GTG GGC CAT CAA GGT ACT GTG CCT AGC GAT AAC ATT GAT
Glu Asp Phe Val Gly His Gln Gly Thr Val Pro Ser Asp Asn Ile Asp

1230
TCA CAA GGG AGG AAT TGT AGT ACA AAT GAC TCA CTG CTG TAA
Ser Gln Gly Arg Asn Cys Ser Thr Asn Asp Ser Leu Leu
```

FIG. 9A

```
                                    30                         15
ATG TCT GAT GCG GCT CCT TCA TTG AGC AAT CTA TTT TAT GAT CCA ACG
Met Ser Asp Ala Ala Pro Ser Leu Ser Asn Leu Phe Tyr Asp Pro Thr 60                                      90
TAT AAT CCT GGT CAA AGC ACC ATT AAC TAC ACT TCC ATA TAT GGG AAT
Tyr Asn Pro Gly Gln Ser Thr Ile Asn Tyr Thr Ser Ile Tyr Gly Asn

120
GGA TCT ACC ATC ACT TTC GAT GAG TTG CAA GGT TTA GTT AAC AGT ACT
Gly Ser Thr Ile Thr Phe Asp Glu Leu Gln Gly Leu Val Asn Ser Thr
                                        TMD1
─────────────────────────────────────────────────────────────────
    150                                      180
GTT ACT CAG GCC ATT ATG TTT GGT GTC AGA TGT GGT GCA GCT GCT TTG
Val Thr Gln Ala Ile Met Phe Gly Val Arg Cys Gly Ala Ala Ala Leu

─────────────────────────────────────────────────────────────────
                    210                                      240
ACT TTG ATT GTC ATG TGG ATG ACA TCG AGA AGC AGA AAA ACG CCG ATT
Thr Leu Ile Val Met Trp Met Thr Ser Arg Ser Arg Lys Thr Pro Ile
                                TMD2
─────────────────────────────────────────────────────────────────
                                270
TTC ATT ATC AAC CAA GTT TCA TTG TTT TTA ATC ATT TTG CAT TCT GCA
Phe Ile Ile Asn Gln Val Ser Leu Phe Leu Ile Ile Leu His Ser Ala
─────────────────────────────────────────────────────────────────
            300                                      330
CTC TAT TTT AAA TAT TTA CTG TCT AAT TAC TCT TCA GTG ACT TAC GCT
Leu Tyr Phe Lys Tyr Leu Leu Ser Asn Tyr Ser Ser Val Thr Tyr Ala

360
CTC ACC GGA TTT CCT CAG TTC ATC AGT AGA GGT GAC GTT CAT GTT TAT
Leu Thr Gly Phe Pro Gln Phe Ile Ser Arg Gly Asp Val His Val Tyr
```

FIG. 9B

TMD3
---

| 390 | | | | | | | | | | 420 | | | |
|---|---|---|---|---|---|---|---|---|---|---|---|---|---|
| GGT | GCT | ACA | AAT | ATA | ATT | CAA | GTC | CTT | CTT | GTG | GCT | TCT | ATT | GAG | ACT |
| Gly | Ala | Thr | Asn | Ile | Ile | Gln | Val | Leu | Leu | Val | Ala | Ser | Ile | Glu | Thr |

| 450 | | | | | | | | | | 480 | | | |
|---|---|---|---|---|---|---|---|---|---|---|---|---|---|
| TCA | CTG | GTG | TTT | CAG | ATA | AAA | GTT | ATT | TTC | ACA | GGC | GAC | AAC | TTC | AAA |
| Ser | Leu | Val | Phe | Gln | Ile | Lys | Val | Ile | Phe | Thr | Gly | Asp | Asn | Phe | Lys |

TMD4
---

| | | | | | 510 | | | | | | | | |
|---|---|---|---|---|---|---|---|---|---|---|---|---|---|
| AGG | ATA | GGT | TTG | ATG | CTG | ACG | TCG | ATA | TCT | TTC | ACT | TTA | GGG | ATT | GCT |
| Arg | Ile | Gly | Leu | Met | Leu | Thr | Ser | Ile | Ser | Phe | Thr | Leu | Gly | Ile | Ala |

| 540 | | | | | | | | | | 570 | | | |
|---|---|---|---|---|---|---|---|---|---|---|---|---|---|
| ACA | GTT | ACC | ATG | TAT | TTT | GTA | AGC | GCT | GTT | AAA | GGT | ATG | ATT | GTG | ACT |
| Thr | Val | Thr | Met | Tyr | Phe | Val | Ser | Ala | Val | Lys | Gly | Met | Ile | Val | Thr |

| | | | | 600 | | | | | | | | | |
|---|---|---|---|---|---|---|---|---|---|---|---|---|---|
| TAT | AAT | GAT | GTT | AGT | GCC | ACC | CAA | GAT | AAA | TAC | TTC | AAT | GCA | TCC | ACA |
| Tyr | Asn | Asp | Val | Ser | Ala | Thr | Gln | Asp | Lys | Tyr | Phe | Asn | Ala | Ser | Thr |

TMD5
---

| 630 | | | | | | | | | | 660 | | | |
|---|---|---|---|---|---|---|---|---|---|---|---|---|---|
| ATT | TTA | CTT | GCA | TCC | TCA | ATA | AAC | TTT | ATG | TCA | TTT | GTC | CTG | GTA | GTT |
| Ile | Leu | Leu | Ala | Ser | Ser | Ile | Asn | Phe | Met | Ser | Phe | Val | Leu | Val | Val |

| | | | | 690 | | | | | | | | | 720 |
|---|---|---|---|---|---|---|---|---|---|---|---|---|---|
| AAA | TTG | ATT | TTA | GCT | ATT | AGA | TCA | AGA | AGA | TTC | CTT | GGT | CTC | AAG | CAG |
| Lys | Leu | Ile | Leu | Ala | Ile | Arg | Ser | Arg | Arg | Phe | Leu | Gly | Leu | Lys | Gln |

FIG. 9C

TMD6
───────────────────────────────────────────────

```
                              750
TTC GAT AGT TTC CAT ATT TTA CTC ATA ATG TCA TGT CAA TCT TTG TTG
Phe Asp Ser Phe His Ile Leu Leu Ile Met Ser Cys Gln Ser Leu Leu
```

```
         780                                     810
GTT CCA TCG ATA ATA TTC ATC CTC GCA TAC AGT TTG AAA CCA AAC CAG
Val Pro Ser Ile Ile Phe Ile Leu Ala Tyr Ser Leu Lys Pro Asn Gln
                                             TMD7
```
───────────────────────────────────────────────
```
                     840
GGA ACA GAT GTC TTG ACT ACT GTT GCA ACA TTA CTT GCT GTA TTG TCT
Gly Thr Asp Val Leu Thr Thr Val Ala Thr Leu Leu Ala Val Leu Ser
```
───────────────────────────────────────────────
```
     870                                 900
TTA CCA TTA TCA TCA ATG TGG GCC ACG GCT GCT AAT AAT GCA TCC AAA
Leu Pro Leu Ser Ser Met Trp Ala Thr Ala Ala Asn Asn Ala Ser Lys
```

```
                         930                             960
ACA AAC ACA ATT ACT TCA GAC TTT ACA ACA TCC ACA GAT AGG TTT TAT
Thr Asn Thr Ile Thr Ser Asp Phe Thr Thr Ser Thr Asp Arg Phe Tyr
```

```
                                 990
CCA GGC ACG CTG TCT AGC TTT CAA ACT GAT AGT ATC AAC AAC GAT GCT
Pro Gly Thr Leu Ser Ser Phe Gln Thr Asp Ser Ile Asn Asn Asp Ala
```

```
         1020                                    1050
AAA AGC AGT CTC AGA AGT AGA TTA TAT GAC CTA TAT CCT AGA AGG AAG
Lys Ser Ser Leu Arg Ser Arg Leu Tyr Asp Leu Tyr Pro Arg Arg Lys
```

```
                     1080
GAA ACA ACA TCG GAT AAA CAT TCG GAA AGA ACT TTT GTT TCT GAG ACT
Glu Thr Thr Ser Asp Lys His Ser Glu Arg Thr Phe Val Ser Glu Thr
```

FIG. 9D

```
      1110                                         1140
GCA GAT GAT ATA GAG AAA AAT CAG TTT TAT CAG TTG CCC ACA CCT ACG
Ala Asp Asp Ile Glu Lys Asn Gln Phe Tyr Gln Leu Pro Thr Pro Thr 1170                                   1200
AGT TCA AAA AAT ACT AGG ATA GGA CCG TTT GCT GAT GCA AGT TAC AAA
Ser Ser Lys Asn Thr Arg Ile Gly Pro Phe Ala Asp Ala Ser Tyr Lys

1230
GAG GGA GAA GTT GAA CCC GTC GAC ATG TAC ACT CCC GAT ACG GCA GCT
Glu Gly Glu Val Glu Pro Val Asp Met Tyr Thr Pro Asp Thr Ala Ala 1260                                        1290
GAT GAG GAA GCC AGA AAG TTC TGG ACT GAA GAT AAT AAT AAT TTA TGA
Asp Glu Glu Ala Arg Lys Phe Trp Thr Glu Asp Asn Asn Asn Leu
```

MAMMALIAN/YEAST HYBRID G PROTEIN-COUPLED RECEPTORS

This application is a divisional of U.S. patent application Ser. No. 07/478,100 filed Feb. 8, 1990, issued as U.S. Pat. No. 5,284,746.

CROSS-REFERENCE TO RELATED APPLICATION

1. Technical Field

The present invention is generally directed toward the expression of proteins, and more specifically, toward the expression of hybrid G protein-coupled receptors in yeast.

2. Background of the Invention

In higher eukaryotic cells, the interaction between ligands (e.g. hormones) and receptors is of central importance in the transmission of and response to extracellular signals. Numerous physiologically important substances elicit cellular responses by binding to and acting on cell surface receptors. Examples of such substances include epinephrine, norepinephrine, isoproterenol and acetylcholine. The ligand-receptor binding mechanism is coupled to an effector mechanism to provide an appropriate cellular response. These mechanisms are often, but not always, combined in a single protein which is integrated into the cell membrane.

One class of receptors requires the presence of proteins which are interposed between the ligand-receptor binding mechanism and the effector mechanism. Upon binding to ligand, receptors of this class interact with guanine nucleotide-binding regulatory proteins (referred to herein as G proteins) which facilitate the transmission of the ligand binding signal (for review see Gilman, *Cell* 36:577–579, 1984 and *Biochemistry* 26:2657–2664, 1987) from the cell surface to the specific cell mechanism(s) to be activated. This class of receptors is generally referred as G protein-coupled receptors.

G protein-coupled receptors mediate important physiological responses, which include vasodilation, stimulation or decrease in heart rate, bronchodilation, stimulation of endocrine secretions and enhancement of gut peristalsis. One group of G protein-coupled receptor, the adrenergic receptors are found in a variety of higher eukaryotic tissues and mediate a diversity of physiological responses (for review see, Lefkowitz et al., *Ann. Rev. Biochem.* 52:159–186, 1983). Ahlquist (*Am. J. Physiol.* 153:586–600, 1948) proposed that adrenergic receptors fall into two classes, α and β, based on the order of activity of a series of ligands. Lands, *Nature* 214:597–598, 1964), Starke (*Revs. Physiol. Biochem. Pharmacol.* 77:1–124, 1977), and Langer et al. (*Biochem. Pharmacol.* 23:1793–1800, 1974) further divided these classes into α1, α2 and β1, β2. Lands (ibid.) designated β1 receptors as those β-adrenergic receptors (referred to herein as βARs) responsible for cardiac stimulation and lipolysis and β2 receptors as those βARs that mediate adrenergic bronchodilation and vasodepression. Ligands to βARs are used in the treatment of anaphylaxis, shock, hypotension, cardiogenic shock, asthma, premature labor, angina, hypertension, cardiac arrhythmias, migraine and hyperthyroidism.

While ligands to G protein-coupled receptors have potential as therapeutic agents, screening for these compounds is both difficult and labor intensive. Currently, ligand binding is measured using radioligand binding methods (Lefkowitz et al., *Biochem. Biophys. Res. Commun.* 60:703–709, 1974; Aurbach et al., *Science* 186:1223–1225, 1974; Atlas et al., *Proc. Natl. Acad. Sci. USA* 71:4246–4248, 1974). Potential agonists can be directly assayed using the radio-ligand binding methods by binding radiolabelled substances to a membrane fraction or to responsive cells. The amount of radioactivity remaining after the excess label is removed is the measure of substance bound to the receptors. Antagonists can be screened by their ability to compete with a known labeled agonist for cell surface receptors, thus reducing the amount of radioactivity bound to the membranes or cell surfaces. In the case of βARs, this method first involves the isolation of intact membranes from responsive tissue or cell lines. Often, only a limited subset of cells is responsive to a particular agent (Lefkowitz et al., *Ann. Rev. Biochem.* 52:159–186, 1983) and such cells may be difficult to grow in culture or may possess a low number of receptors, making assays cumbersome. In addition, mammalian cells co-express a variety of G protein-coupled receptor classes and subclasses making ligand screening for any one particular class of receptors difficult. The current assay system is labor intensive and does not lend itself to automation and high through-put screening assays. The use of cultured mammalian tissues as a source of receptors is both difficult and expensive.

Although human βARs have been expressed in *E. coli* (Marullo et al., *Proc. Natl. Acad. Sci. USA* 85:7551–7555, 1988; and Marullo et al., *Bio/Technology* 7:923–927, 1989), the level of receptor expression is very low and ligand binding assays are limited to the multiple-step, labor-intensive radioligand assay used for mammalian cells. As such, these transformed cells are not useful for commercial scale, high through-put ligand screening.

There is therefore a need in the art for an assay system which permits high volume screening of compounds which may act on higher eukaryotic cells via G protein-coupled receptors. Such a system should be rapid, inexpensive and adaptable to high volume screening. The present invention provides such an assay system and further provides other related advantages.

SUMMARY OF THE INVENTION

Briefly stated, the present invention discloses DNA sequences encoding hybrid G protein-coupled receptors. These hybrid G protein-coupled receptors, when expressed in appropriate host cells, allow screening of potential ligands to mammalian G protein-coupled receptors using a standardized method. The invention also provides a variety of methods for detecting the presence of ligand in a test substance all using a single cell type, thus providing for standardized detection methods not previously available in the art. The host cells of the present invention provide the further advantages of being easily cultured and respond to ligands in an easily monitored manner.

In one aspect of the invention DNA sequences encoding hybrid G protein-coupled receptor are disclosed wherein the receptor comprises a mammalian G protein-coupled receptor having at least one domain other than the ligand-binding domain replaced with a corresponding domain of a yeast G protein-coupled receptor. In one embodiment of the invention, the yeast G protein-coupled receptor is selected from the group consisting of the *Saccharomyces cerevisiae* STE2 gene product, the *Saccharomyces cerevisiae* STE3 gene product and the *Saccharomyces kluyveri* STE2 gene product. In a preferred embodiment, the yeast G protein-coupled receptor is the *Saccharomyces cerevisiae* . STE2 gene product. In another embodiment of the invention, the mammalian G protein-coupled receptor is selected from the group consisting of β-adrenergic receptors, α-adrenergic receptors, muscarinic receptors, angiotensin receptors, substance K receptors and rhodopsin. In one embodiment, the DNA sequence encodes a hybrid mammalian G protein-coupled receptor wherein the mammalian G protein-coupled receptor domain selected from the group consisting of the extracellular amino-terminal domain, the effector domain, the third internal effector domain and the carboxy-terminal internal effector domain is replaced with the corresponding domain of a yeast G protein-coupled receptor. In another embodiment of the invention, the DNA sequence encodes a hybrid mammalian G protein-coupled receptor wherein the mammalian G protein-coupled receptor domains selected from the group consisting of the extracellular amino-terminal and effector domains of the mammalian G protein-coupled receptor are replaced with the extracellular amino-terminal and effector domains of a yeast G protein-coupled receptor. In yet another embodiment, the DNA sequence encodes a hybrid mammalian G protein-coupled receptor wherein the mammalian G protein-coupled receptor domains selected from the group consisting of the carboxy-terminal internal effector domain, the third internal effector domain, and the carboxy-terminal internal effector and third internal effector domains are replaced by the corresponding domains of a yeast G protein-coupled receptor.

Another aspect of the invention is directed towards a DNA construct capable of directing the expression of a biologically active hybrid G protein-coupled receptor in a yeast cell, comprising the following operatively linked elements: a transcriptional promoter; a DNA sequence encoding a biologically active hybrid G protein-coupled receptor, said receptor comprising a mammalian G protein-coupled receptor having at least one domain other than the ligand-binding domain replaced with the corresponding domain of a yeast G protein-coupled receptor; and a transcriptional terminator.

In a related aspect, the present invention discloses yeast host cells transformed with a DNA construct capable of directing the expression of a biologically active hybrid G protein-coupled receptor, said receptor comprising a mammalian G protein-coupled receptor having at least one domain other than the ligand-binding domain replaced with the corresponding domain of a yeast G protein-coupled receptor. In a preferred embodiment, the yeast host cell is a *Saccharomyces cerevisiae* cell. In a particularly preferred embodiment, the yeast host cell is a *Saccharomyces cerevisiae* a haploid cell that does not contain functional BAR1 gene. In another aspect of the invention, the yeast host cell is transformed with a second DNA construct comprising the BAR1 promoter operatively linked to an indicator DNA sequence, and wherein the second DNA construct is integrated at the BAR1 locus. In a preferred embodiment, the indicator DNA sequence is the lacZ coding sequence.

The present invention discloses methods for detecting the presence of ligand in a test substance. The methods comprise the steps of a) exposing a culture of yeast host cells transformed with a DNA construct capable of directing the expression of a biologically active hybrid G protein-coupled receptor having at least one domain other than the ligand-binding domain replaced with a corresponding domain of a yeast G protein-coupled receptor, and wherein said yeast host cells express the biologically active hybrid G protein-coupled receptor, to a test sample under suitable conditions to allow binding of ligand to the hybrid G protein-coupled receptor; and b) detecting a biological response of the host cell and therefrom determining the presence of the ligand. In one embodiment of the invention, the host cells are also transformed with a second DNA construct comprising the BAR1 promoter operatively linked to an indicator DNA sequence and the step of detecting comprises detecting the expression of said indicator DNA sequence. In a preferred embodiment, the method further comprises host cells that are *Saccharomyces cerevisiae* a haploid cells transformed with a second DNA construct comprising the BAR1 promoter operatively linked to the *E. coli* lacZ coding sequence wherein the second DNA construct is integrated at the BAR1 locus. In one embodiment of the invention, the method further comprises host cells that are suspended in an agar overlay on top of an appropriate solid growth medium. In related aspect of the invention, the agar overlay includes one or more wells and the step of exposing comprises filling the wells with the test substance. In another embodiment of the invention, the step of exposing comprises placing a filter saturated with the test substance onto the agar overlay. In one preferred embodiment, the method comprises host cells that are *Saccharomyces cerevisiae* mating-type a haploid cell transformed with a DNA construct capable of directing the expression of a hybrid G protein-coupled receptor, wherein the receptor comprises a mammalian G protein-coupled receptor having at least one domain other than the ligand-binding domain replaced with a corresponding domain of a STE2 gene product, and wherein the step of detecting comprises detecting the presence of a halo of host cells arrested in the G1 phase of cell division. In another embodiment of the invention, the method comprises a culture of host cells suspended with an agonist in an agar overlay on top of an appropriate solid growth medium. In preferred embodiment of the invention, the method comprises *Saccharomyces cerevisiae* mating-type a host cells transformed with a DNA construct capable of directing the expression of a hybrid G protein-coupled receptor, wherein the receptor comprises a mammalian G protein-coupled receptor having at least one domain other than the ligand-binding domain replaced with a corresponding domain of a STE2 gene product, suspended with an agonist in an agar overlay on top of an appropriate solid growth medium, and wherein the step of detecting comprises detecting the presence of a halo of host cell colonies.

Other aspects of the invention will become evident upon reference to the following detailed description and attached drawings.

Symbols used are B, Bam HI; E, Eco RI; H, Hind III; P, Pst I; Pv, Pvu II; S, Sal I; X, Xba I; subP, substance P. Open boxes indicates vector sequences, the hatched box refers to M13mp8 vector sequences.

FIGS. 3A, 3B, and 3C illustrates a nucleotide sequence encoding a representative hamster G protein-coupled receptor, the hamster $\beta_2AR$ and the inferred amino acid sequence of the protein. Numbers above the line refer to the nucleotide sequence of the mature protein. Boxed sequences refer to the second and third external ligand-binding domains. Symbols L2 and L4 refer to the first, second and third external ligand-binding domains, respectively.

Figure 4:
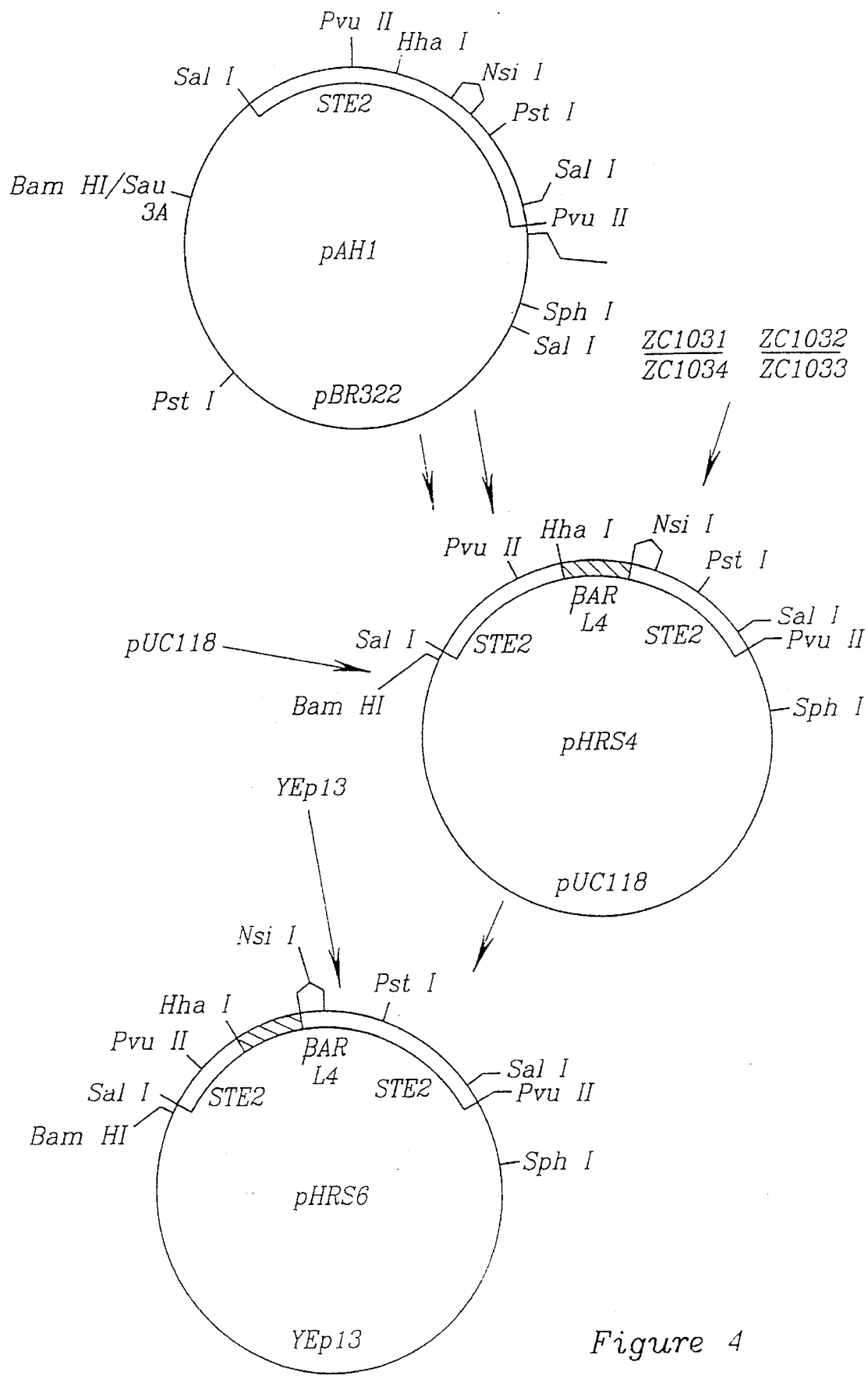

FIG. 4 illustrates the construction of plasmid pHRS6. Symbols used are as in FIG. 1, and STE2, *Saccharomyces cerevisiae* STE2 genomic sequence.

Figure 5:
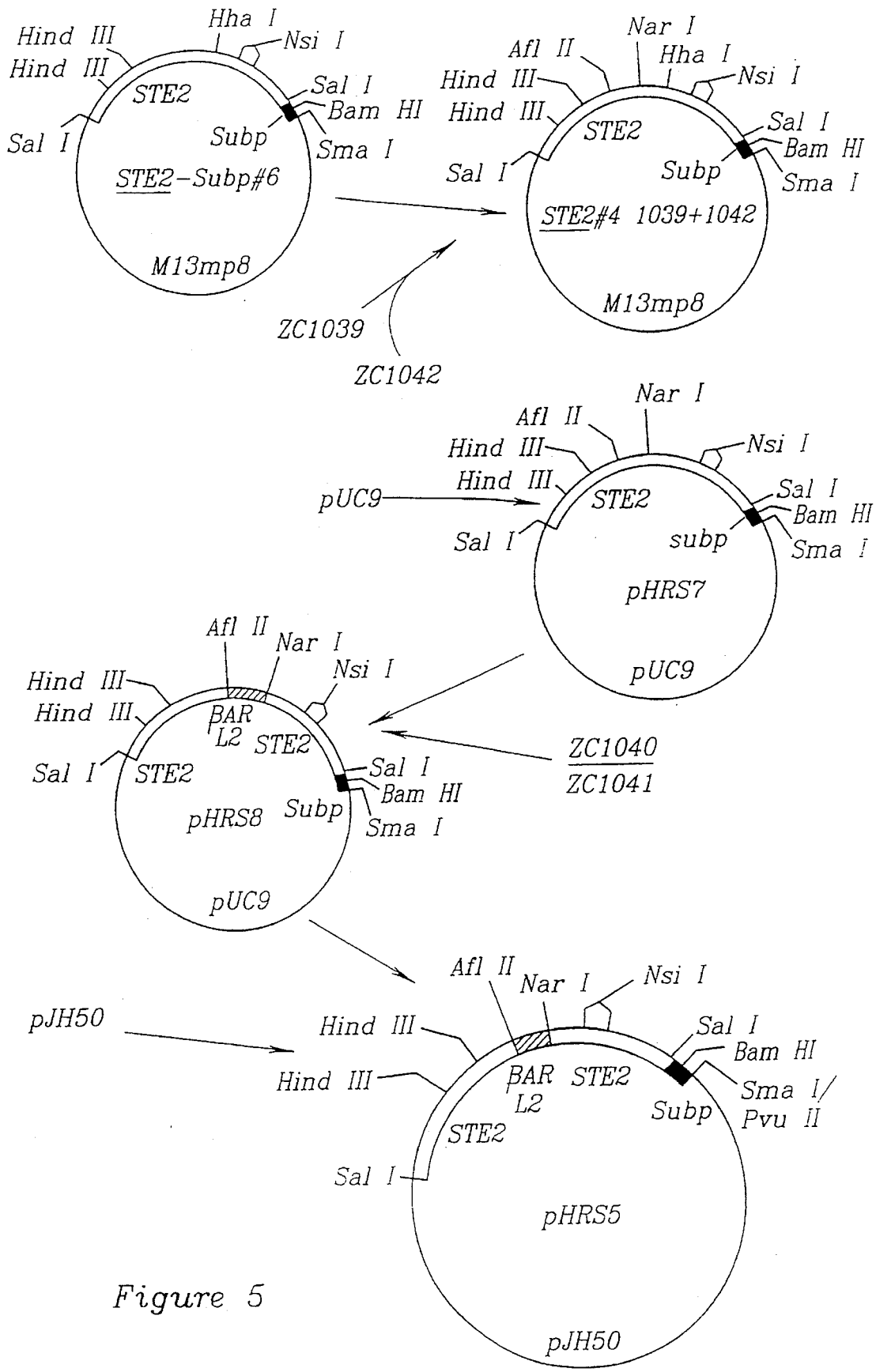

FIG. 5 illustrates the construction of plasmid pHRS5. Symbols used are as in FIG. 1, and STE2, *Saccharomyces cerevisiae* STE2 genomic sequence; subP, substance P C-terminal pentapeptide dimer coding sequence.

Figure 6:
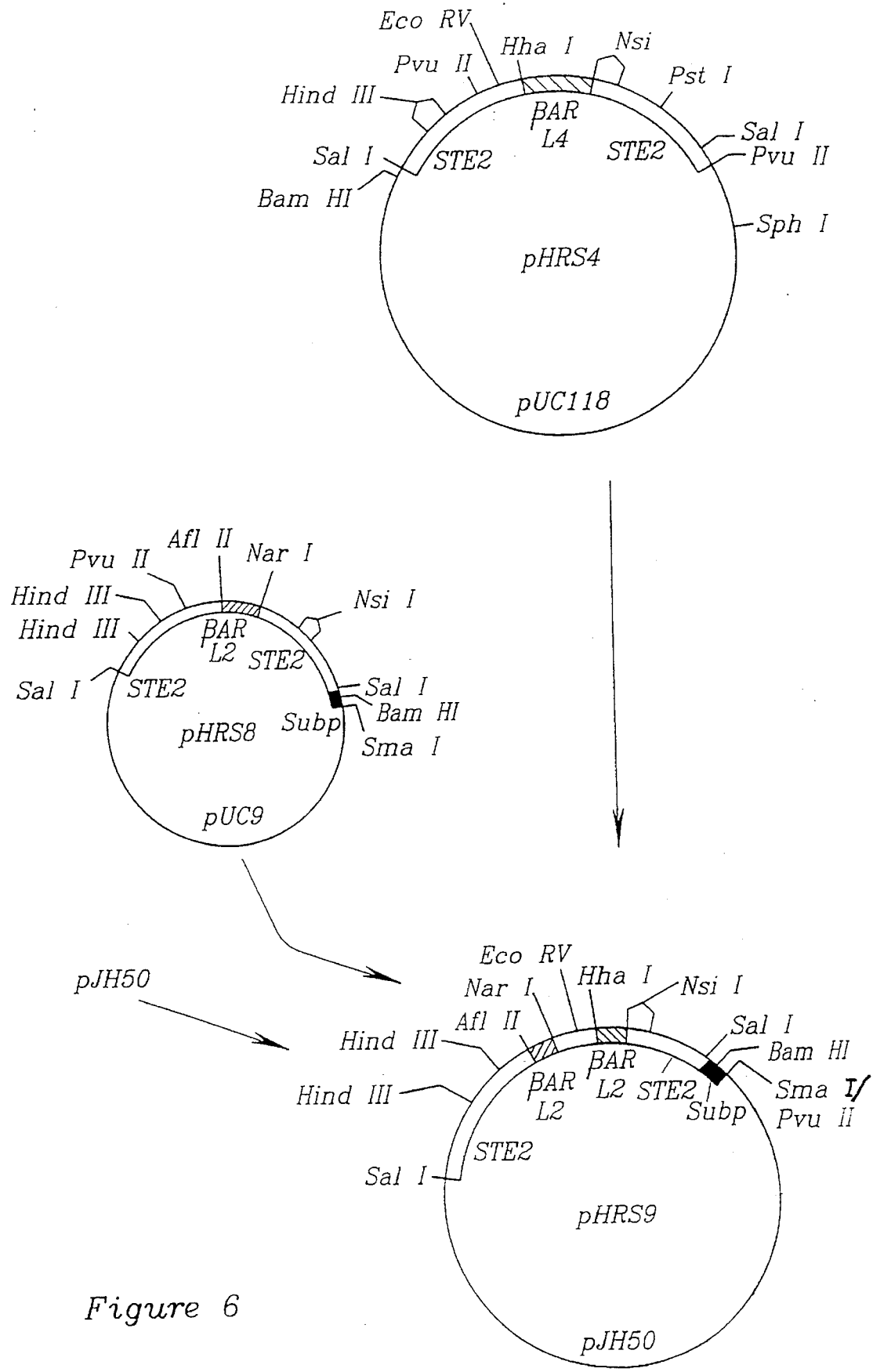

FIG. 6 illustrates the construction of plasmid pHRS9. Symbols used are as in FIG. 1, and STE2, *Saccharomyces cerevisiae* STE2 genomic sequence; subP, substance P C-terminal pentapeptide dimer coding sequence.

FIGS. 7A, 7B, 7C, and 7D illustrates a nucleotide sequence encoding a representative human G protein-coupled receptor, the human $\beta_2AR$ and the inferred amino acid sequence of the protein. Numbers above the line refer to the nucleotide sequence of the mature protein. Solid lines above the sequence refer to the putative transmembrane domains. Symbols used are as for FIG. 1.

Figure 8:
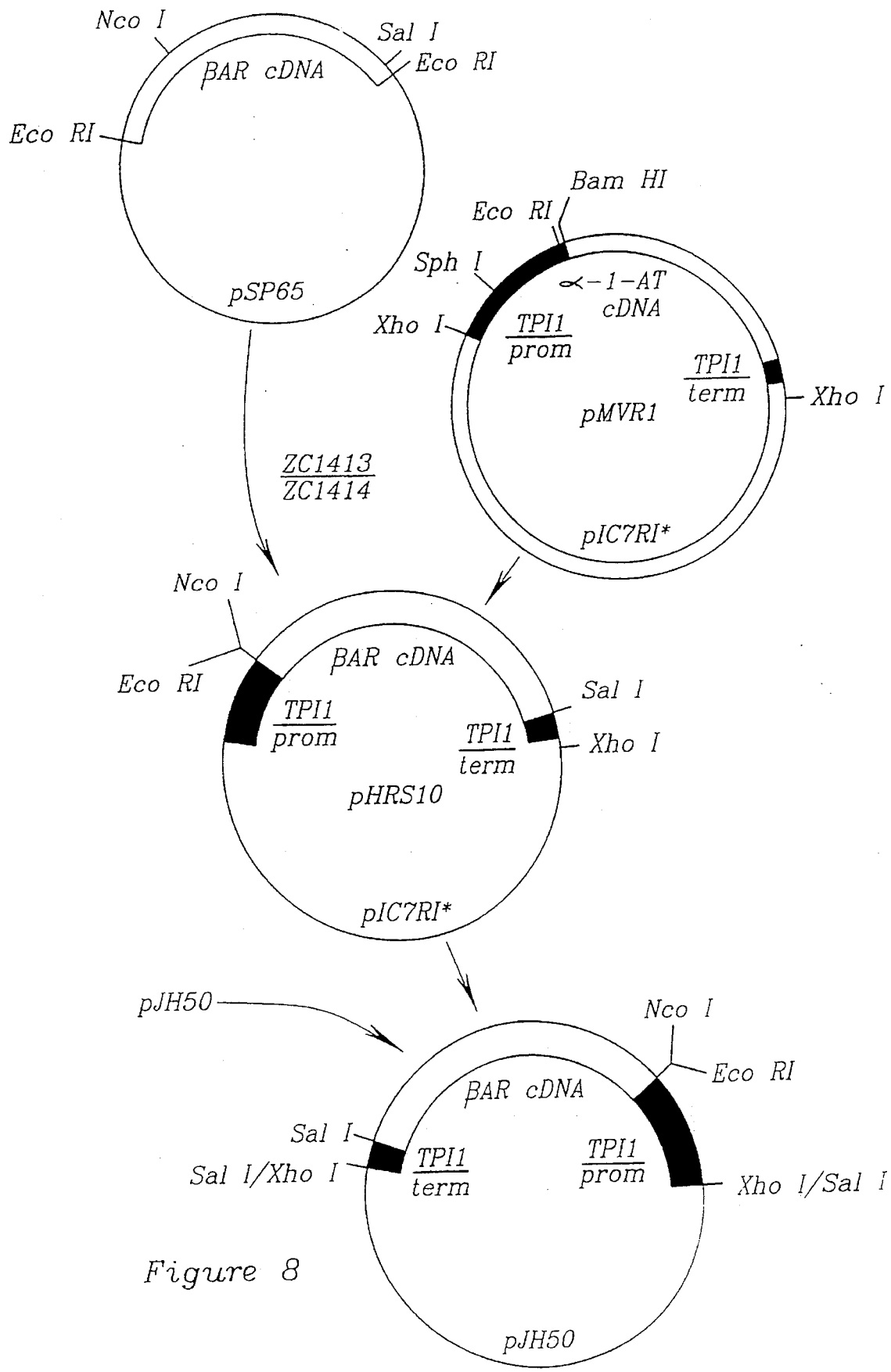

FIG. 8 illustrates the construction of plasmid pHRS11.

FIGS. 9A, 9B, 9C, and 9D illustrates a nucleotide sequence encoding a representative yeast G protein-coupled receptor, the *Saccharomyces cerevisiae* STE2 gene and the inferred amino acid sequence of the protein. Numbers above the line refer to the nucleotide sequence of the mature protein. Solid lines above the sequence refer to the putative transmembrane domains. Symbols used are as for FIG. 1.

Figure 10A:
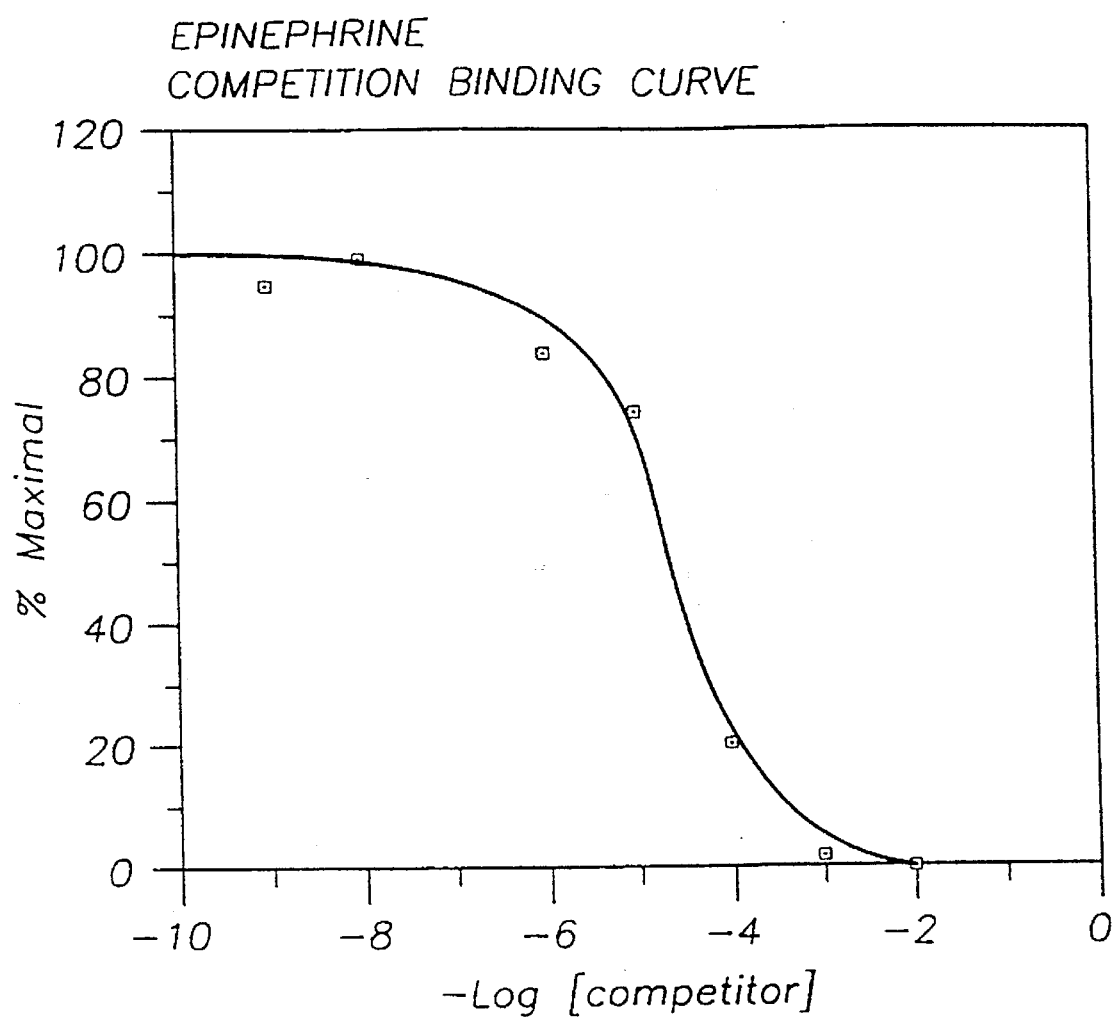
Figure 10B:
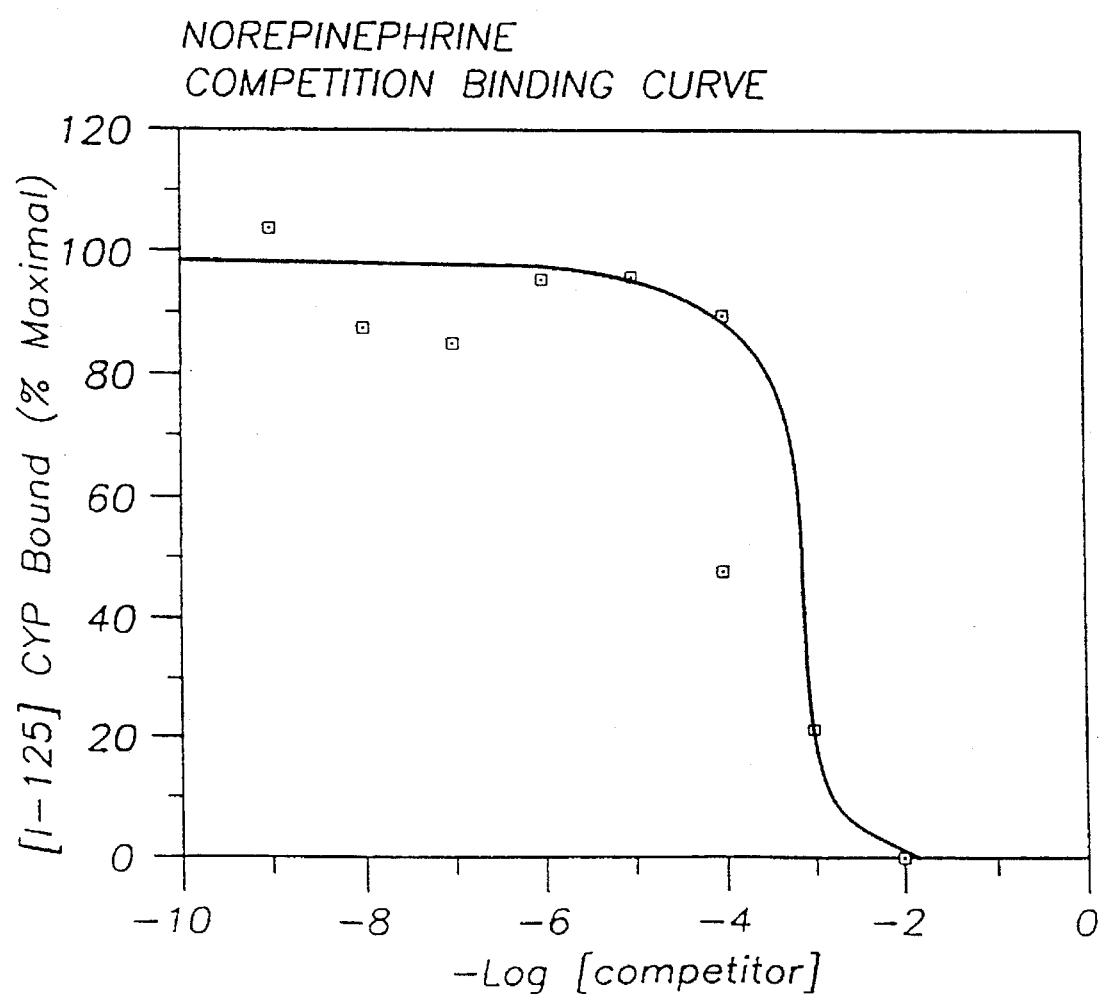

FIG. 10 illustrates competitive binding curves for epinephrine and norepinephrine.

Figure 11:
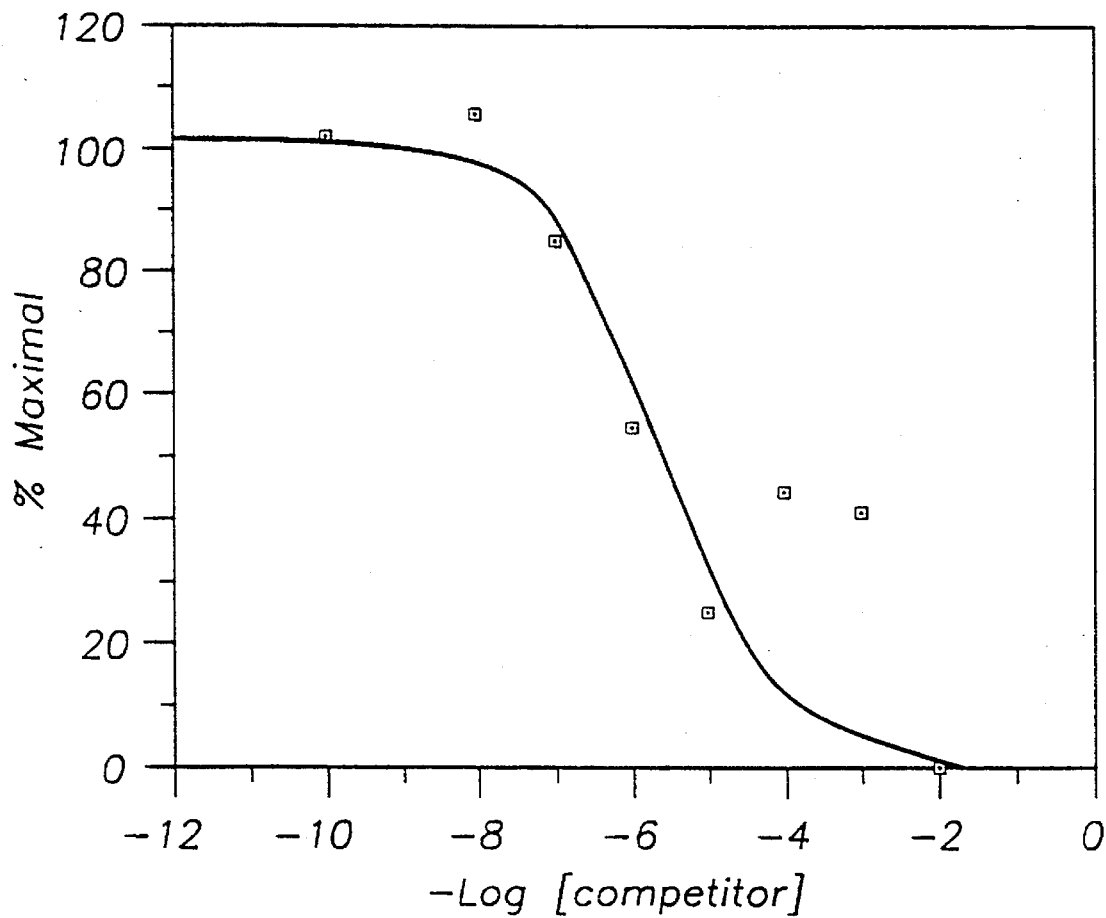

FIG. 11 illustrates a competitive binding curve to isoproterenol.

DETAILED DESCRIPTION OF THE INVENTION

Prior to setting forth the invention, it may be helpful to an understanding thereof to set forth definitions of certain terms to be used hereinafter.

Biological activity: A function or set of activities performed by a molecule in a biological context (i.e., in an organism or an vitro facsimile thereof). Biological activities may include the induction of extracellular matrix secretion from responsive cell lines, the induction of hormone secretion, the induction of chemotaxis, the induction of differentiation, or the inhibition of cell division of responsive cells. A recombinant protein is considered to be biologically active if it exhibits one or more biological activities of its native counterpart.

A receptor is considered to be biologically active if it is capable of binding ligand, transmitting a signal and eliciting a cellular response. A yeast-expressed mammalian hybrid G protein-coupled receptor having a domain other than the ligand-binding domain replaced with a corresponding domain of a yeast pheromone receptor, for example, is biologically active if it is capable of binding ligand and inducing the mating response pathway, resulting in the G1 arrest of the yeast host cells.

Ligand: A molecule capable of being bound by the ligand-binding domain of a receptor. The molecule may be chemically synthesized or may occur in nature.

Domain: A portion of a protein or peptide that is physically or functionally distinguished from other portions of the protein or peptide. Physically-defined domains include those amino acid sequences that are exceptionally hydrophobic or hydrophilic, such as those sequences that are membrane-associated or cytoplasm-associated. Domains may also be defined by internal homologies that arise, for example, from gene duplication. Functionally-defined domains have a distinct biological function(s). The ligand-binding domain of a receptor, for example, is that domain that binds ligand. Functionally-defined domains need not be encoded by contiguous amino acid sequences. Functionally-defined domains may contain one or more physically-defined domain. Receptors, for example, are generally divided into the ligand-binding domain and an effector domain. G protein-coupled receptors are generally divided into an extracellular amino-terminal domain, a ligand-binding domain, and an effector domain.

As noted above, a variety of physiological responses of higher eukaryotic cells are mediated by G protein-coupled receptors. Ligands to these receptors are used to treat a variety of conditions. Currently available methods for screening potential G protein-coupled receptor ligands are expensive, labor intensive and are limited by the necessity of isolating membrane fragments from responsive tissues or cell lines.

The present invention provides hybrid G protein-coupled receptors. These hybrid receptors comprise a mammalian G protein-coupled receptor having at least one domain other than the ligand-binding domain replaced with a corresponding domain of a yeast G protein-coupled receptor. The invention further provides DNA constructs capable of directing the expression of such DNA sequences, eukaryotic cells transformed with such DNA constructs, and methods for assaying ligand binding using such cells. The invention thus provides cross-species hybrid G protein-coupled receptors not previously known.

Figure 1:
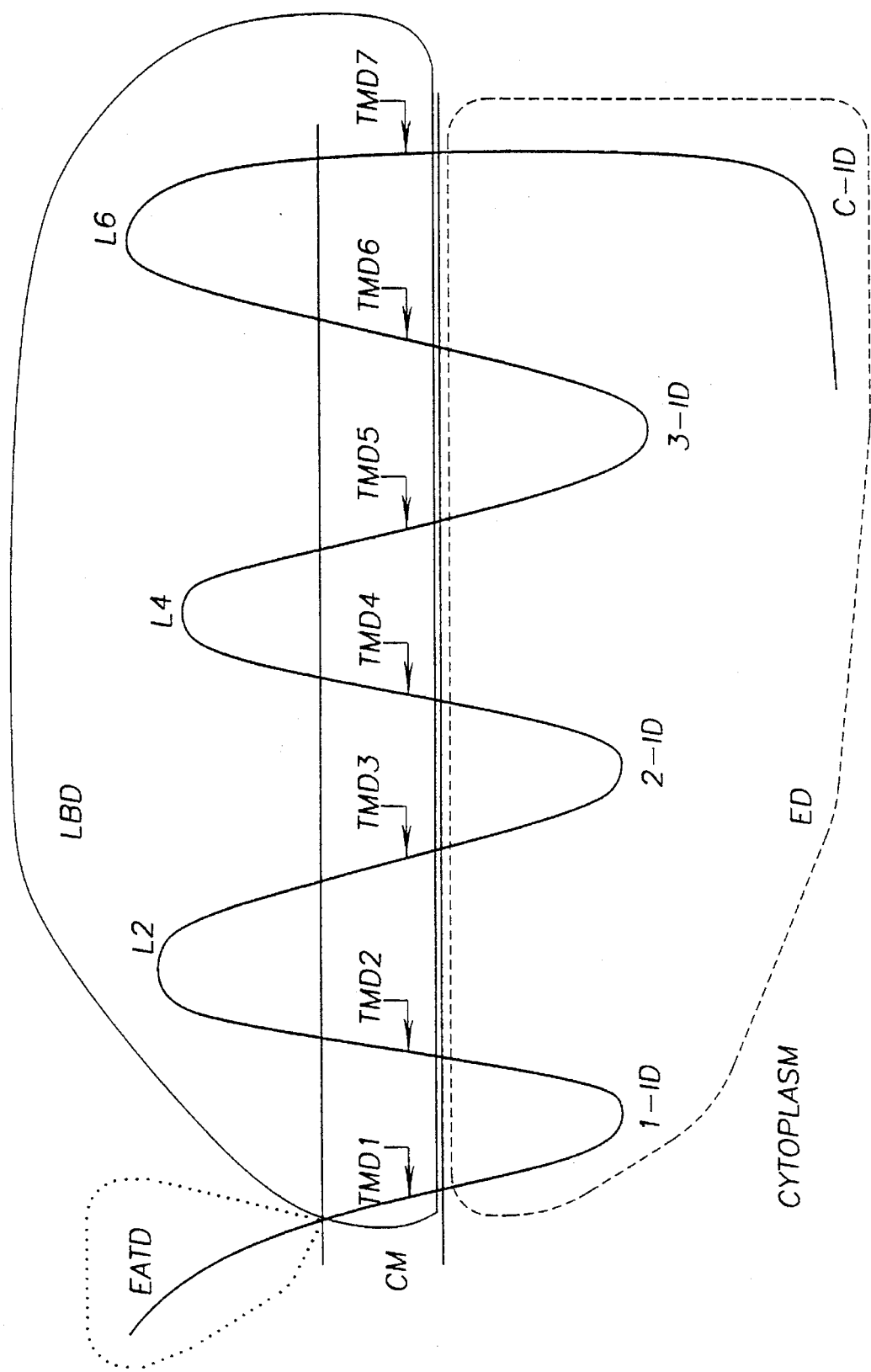
FIG. 1 illustrates the structure of a representative G protein-coupled receptor. Symbols used are EATD, which is encircled by the dotted line, extracellular amino-terminal domain; LBD, which is encircled by the solid line, the ligand-binding domain; ED, which is encircled by the dashed line, the effector domain; 1-ID, the first internal effector domain; 2-ID, the second internal effector domain; 3-ID, the third internal effector domain; C-ID, the carboxy-terminal internal effector domain; L2, the first external ligand-binding domain; L4, the second external ligand-binding domain; L6, the third external ligand-binding domain; TMD1, the first transmembrane domain; TMD2, the second transmembrane domain; TMD3, the third transmembrane domain; TMD4, the fourth transmembrane domain; TMD5, the fifth transmembrane domain; TMD6, the sixth transmembrane domain, and TMD7, the seventh transmembrane domain.

While not wishing to be bound by a graphical representation, G protein-coupled receptors are believed to have the general structure shown in FIG. 1. These receptors comprise an extracellular amino-terminal domain, a ligand-binding domain and an effector domain (FIG. 1). Comparisons of avian and mammalian $\beta$-adrenergic receptor cDNA's (Yarden et al., *Proc. Natl. Acad. Sci. USA* 83:6795–6799, 1986; Dixon et al., *Nature* 321:75–79, 1986; and Kobilka et al., *Proc. Natl. Acad. Sci. USA* 84:46–50, 1987), a bovine rhodopsin cDNA (Nathans and Hogness, *Cell* 34:807–814, 1983), an $\alpha_2$-adrenergic receptor (Kobilka et al., *Science* 238:650–656, 1987), an angiotensin receptor cDNA (Young et al., *Cell* 45:711–719, 1986; Jackson et al., *Nature* 335:437–439, 1988), a bovine substance K receptor (Masu et al., *Nature* 329:836–838, 1987), and a muscarinic acetylcholine receptor cDNA (Kubo et al., *Nature* 323:411–416, 1986) predict that all six proteins share the structure shown in FIG. 1 (for review see Lefkowitz et al., *J. Biol. Chem.* 263:4993–4996, 1988; Panayotou and Waterfield, *Curr Opinion Cell Biol.* 1:167–176, 1989).

As used herein, the ligand-binding domain of a G protein-coupled receptor is that portion of the receptor, shown in FIG. 1 as LBD, that is involved in binding ligand and generally comprises that portion of the receptor containing the transmembrane domains (TMDs) and their associated extracellular ligand-binding domains. The structure of G protein-coupled receptors may be predicted from the primary translation products using the hydrophobicity plot function of, for example, P/C Gene or Intelligenetics Suite (Intelligenetics, Mt. View, Calif.) or may be predicted according to the methods described, for example, by Kyte and Doolittle, *J. Mol. Biol.* 157:105–132, 1982). The ligand-binding domain of the $\beta_2$-adrenergic receptor, for example, has been shown to require at least the third, fifth, and seventh transmembrane domains (Dixon et al., *Nature* 326:73–77, 1987; Strader et al., *J. Biol. Chem.* 263:10267–10271, 1988; Strader et al., *J. Biol. Chem.* 264:13572–13578, 1989). The effector domain of a G protein-coupled receptor, shown in FIG. 1 as ED, is that domain of a G protein-coupled receptor that may be phosphorylated and may be involved in the interaction with associated G proteins and in the mechanisms of desensitization, adaptation, internalization and recycling of the receptor-ligand complex. The effector domain is understood to be encoded by amino acid sequences that need not be contiguous and may include the first, second, third and/or carboxy-terminal internal effector domains (FIG. 1 as 1-ID, 2-ID, 3-ID and C-ID, respectively). Dixon et al. (ibid., 1987), for example, have suggested that the effector domain of a human $\beta_2$AR includes the third cytoplasmic domain.

The present invention makes use of the ability of eukaryotic cells to respond to stimuli via G protein-coupled receptors. In one embodiment of the invention, for example, DNA sequences encoding hybrid G protein-coupled receptors, when expressed in yeast host cells, enable the host cells to bind and respond, through a yeast biological response, to G protein-coupled receptor ligands that would not otherwise elicit a such a response. A representative such response is that of yeast cells to mating pheromones. Cells of the yeasts *Saccharomyces cerevisiae* and *Saccharomyces kluyveri* are responsive to the external mating pheromones α-factor and a-factor. *Saccharomyces cerevisiae* and *Saccharomyces kluyveri* MATa cells express STE2 gene products that have been shown to be the α-factor receptor (Jenness et al., *Cell* 35:521–529, 1983; Nakayama et al., *EMBO J.* 4:2643–2648, 1985; Burkholder and Hartwell, *Nuc. Acids Res.* 13:8463–8475, 1985; Marsh and Herskowitz, *Proc. Natl. Acad. Sci. USA* 85:3855–3859, 1988). *Saccharomyces cerevisiae* MATα cells, express the STE3 gene product which has been shown to be the a-factor receptor (Nakayama et al., *EMBO J.* 4:2643–2648, 1985; Hagen et al., *Proc. Natl. Acad. Sci. USA* 83:1418–1422, 1986). Although the mechanism(s) by which these putative receptors mediate cellular responses has not been elucidated, it is generally believed that these receptors are coupled to G-proteins (Whiteway et al., *Cell* 56:467–477, 1989; Herskowitz and Marsh, *Cell* 50:995–996, 1987). The binding of mating pheromones to their respective receptors activates the mating pheromone response pathway. The response pathway is believed to be mediated, in part, by the SCG1, STE4 and STE18 gene products and leads to the transcriptional induction of mating-type specific genes and agglutinin genes, and to the arrest of cells in the G1 phase of cell division. The present invention utilizes DNA sequences encoding hybrid G protein-coupled receptors that, when expressed by yeast host cells, enable the host cells to bind and respond to G protein-coupled receptor ligands that would not otherwise elicit a yeast mating response.

DNA sequences encoding hybrid G protein-coupled receptors may be prepared from cloned receptor DNAs using standard techniques of restriction enzyme digestion, exonuclease digestion and ligation or may be prepared by in vitro mutagenesis using, for example, the method described by Zoller and Smith (*DNA* 3:479–488, 1984) or Kunkel (*Proc. Nat. Acad. Sci. USA* 82:488–492, 1985) to replace the DNA sequence encoding at least one domain, other than the ligand-binding domain, of a mammalian G protein-coupled receptor with the DNA sequence encoding the corresponding domain of a yeast G protein-coupled receptor. One exemplary DNA sequence encoding a hybrid G protein-coupled receptor encodes a hybrid human $\beta$AR wherein the amino-terminal extracellular domain is replaced with the amino-terminal extracellular domain of the *Saccharomyces cerevisiae* STE2 gene product. Another exemplary DNA sequence encoding a hybrid G protein-coupled receptor encodes a hybrid human $\beta$AR wherein the carboxy-terminal internal effector domain is replaced with the carboxy-terminal internal effector domain of the *Saccharomyces cerevisiae* STE2 gene product. Another exemplary DNA sequence encoding a hybrid G protein-coupled receptor encodes a hybrid human $\beta$AR wherein the amino-terminal extracellular and carboxy-terminal internal effector domains are replaced with the amino-terminal extracellular and carboxy-terminal internal effector domains of the *Saccharomyces cerevisiae* STE2 gene product. Another exemplary DNA sequence encoding a hybrid G protein-coupled receptor encodes a hybrid human $\beta$AR wherein the amino-terminal extracellular domain, the third internal effector domain and carboxy-terminal internal effector domain are replaced with the amino-terminal extracellular domain, the third internal effector domain and carboxy-terminal internal effector domain of the *Saccharomyces cerevisiae* STE2 gene product.

Complementary DNAs encoding a human $\beta_2$AR (Kobilka et al., ibid.), a human $\beta_1$AR (Frielle et al., *Proc. Natl. Acad. Sci. USA* 84:7920–7924, 1987), a hamster $\beta_2$AR (Dixon et al., ibid., 1986), a turkey $\beta$AR (Yarden et al., ibid.), a rhodopsin (Nathands and Hogness, ibid.), an a$\beta_2$-adrenergic receptor (Kobilka et al., ibid., 1987), an angiotensin receptor (Young et al., ibid.; Jackson et al., ibid.), a substance K receptor (Masu et al., ibid.), and a muscarinic acetylcholine receptor (Kubo et al., ibid.) have been described. Alternatively, these and other G protein-coupled receptor DNAs may be cloned from cDNA libraries prepared from appropriate cell lines and isolated by homology to cloned genomic or cDNA sequences encoding G protein-coupled receptors or using antibodies directed against the receptor. Alternatively cDNA libraries may be constructed into expression vectors and G-protein-coupled receptor DNAs may be isolated by the identification of cells expressing the G protein-coupled receptor. DNA sequences encoding mammalian G protein-coupled receptors may also be synthesized using standard techniques. In general, cDNA sequences are preferred for carrying out the present invention due to their lack of intervening sequences which can lead to aberrant RNA processing and reduced expression levels, particularly in yeast cells. Complementary DNAs encoding a $\beta_2$AR, for example, may be obtained from libraries prepared from placental cells according to standard laboratory procedures and screened using genomic or cDNA sequences of known $\beta_2$ARs. If partial clones are obtained, it is necessary to join them in proper reading frame to produce a full length clone, using such techniques as endonuclease cleavage, ligation, and loop-out mutagenesis.

DNA sequences encoding yeast G protein-coupled receptors also have been described. For example, the *Saccharomyces cerevisiae* STE2 gene (Nakayama et al., *EMBO J.*

4:2643–2648, 1985; Burkholder and Hartwell, *Nuc. Acids Res.* 13:8463–8475, 1985), the *Saccharomyces cerevisiae* STE3 gene (Nakayama et al., *EMBO J.* 4:2643–2648, 1985; Hagen et al., *Proc. Natl. Acad. Sci. USA* 83:1418–1422, 1986 and Hagen et al., *Proc. Natl. Acad. Sci. USA* 83:1418–1422, 1986) and the *Saccharomyces kluyveri* STE2 gene (Marsh and Herskowitz, *Proc. Nat. Acad. Sci. USA* 85:3855–3859, 1988) have been described. DNA sequences encoding yeast G protein-coupled receptors may be cloned from DNA libraries prepared from yeast strains using the standard yeast techniques of transformation and complementation. The *Saccharomyces cerevisiae* STE2 gene, for example, may be cloned using a DNA library prepared from wild type yeast cells to transform a *Saccharomyces cerevisiae* strain carrying a ste2 mutation. DNA sequences capable of complementing the ste2 mutation will enable the yeast host cells to mate.

DNA sequences encoding the hybrid receptor fusions are placed in suitable expression vectors for expression eukaryotic cells such as in yeast. Suitable yeast expression vectors include YRp7 (Struhl et al., *Proc. Natl. Acad. Sci. USA* 7:1035–1039), YEp13 (Broach et al. *Gene* 8:121–133, 1979), pJDB248 and pJDB219 (Beggs, ibid.) and derivatives thereof. Such vectors will generally include a selectable marker, such as the nutritional marker LEU2, which allows selection in a yeast host strain carrying a leu2 mutation. Another selectable marker that may be used is the POT1 gene described by Kawasaki and Bell (EP 171,141) that allows complementation of tpi1 mutations which render the host cell unable to grow in the presence of glucose.

Preferred promoters in yeast expression vectors include promoters from the *Saccharomyces cerevisiae* STE2 and STE3 genes (Hartig et al., *Mol. Cell Biol.* 6:2106–2114, 1986; Nakayama et al., ibid.), *Saccharomyces cerevisiae* glycolytic genes (Hitzeman et al. *J. Biol. Chem.* 255:12073–12080, 1980; Alber and Kawasaki, *J. Mol. Appl. Genet.* 1:419–434, 1982) or *Saccharomyces cerevisiae* alcohol dehydrogenase genes (Young et al., in *Genetic Engineering of Microorganisms for Chemicals*, Hollaender et al., (eds), p. 335, Plenum, N.Y., 1982; Ammerer, *Meth Enzymol.* 101:192–201, 1983). A particularly preferred promoter is the *Saccharomyces cerevisiae* TPI1 promoter (Alber and Kawasaki, ibid.; Kawasaki, U.S. Pat. No. 4,599,311). In addition, it is preferable to include a transcriptional termination signal, such as the TPI1 terminator, within the expression vector.

A number of eukaryotic cells may be used in the present invention. Preferred eukaryotic host cells for use in carrying out the present invention are strains of the yeast. Techniques for transforming yeast are well known in the literature, and have been described, for instance, by Beggs (*Nature* 275:104–108, 1978) and Hinnen et al. (*Proc. Natl. Acad. Sci. USA* 75:1929–1933, 1984). Particularly preferred yeast host cells for use in the present invention are strains of *Saccharomyces cerevisiae*. In one embodiment of the invention, *Saccharomyces cerevisiae* cells that are MATa and do not produce a functional STE2 gene product are used as host cells. In a preferred embodiment, the *Saccharomyces cerevisiae* host cells are MATa cells containing a deletion of some or all of the STE2 gene. In another embodiment of the invention, the *Saccharomyces cerevisiae* host cells are MATα cells containing a genetic deficiency in the BAR1 gene. In a preferred embodiment of the invention, the *Saccharomyces cerevisiae* host cell are MATa cells containing a deletion of the BAR1 gene. In a particularly preferred embodiment of the invention the *Saccharomyces cerevisiae* host cells are MATa cells containing a deletion of the STE2 gene and a deletion of the BAR1 gene wherein the *E. coli* lacZ gene operatively linked to the BAR1 promoter replaces some or all of the BAR1 coding region. Suitable host strains may be obtained from depositories such as American Type Culture Collection, Rockville, Md., and the Yeast Genetic Stock Center, Berkeley, Calif., or may be prepared using standard mutagenesis techniques. Yeast host strains containing gene disruptions may be prepared, for example, by the method essentially described by Rothstein (*Meth. Enzymology* 101:202–211, 1983).

Transformed yeast host cells are obtained by selecting for the presence of the selectable marker. In general, selection of transformed cells is accomplished by complementation of the host's genetic defect by the selectable marker present on the plasmid. Yeast host cells that are genetically leu2 and are transformed with vectors carrying the LEU2 marker, for example, are generally grown in a selective medium lacking the amino acid leucine.

After selection, the cells are grown in an appropriate growth medium to begin expressing the gene of interest. As used herein, the term "appropriate growth medium" means a medium containing nutrients and other components required for the selection and growth of transformed cells, and the expression of the DNA sequences encoding the hybrid G protein-coupled receptor. Media generally include a carbon source, a nitrogen source, essential acids, essential sugars, vitamins and salts. Media requirements will vary somewhat for particular host strains. Selection of an appropriate growth medium is within the level of ordinary skill in the art. In one embodiment, the medium is supplemented with 5-bromo-4-chloro-3-indolyl-β-D-galactoside (X-gal) and the pH of the medium is preferably maintained at a pH greater than 6.8 and less than 7.0. A stable pH may be maintained by buffering the medium. Suitable buffering agents include succinic acid, Bis-Tris (Sigma Chemical Co., St. Louis, Mo.) and potassium phosphate. The X-gal is preferably supplemented at a concentration of 40 µg/ml. In some cases, solid growth medium may be required. An appropriate solid growth medium may be prepared for any appropriate growth medium by supplementing the media with between 1% and 3% agar, preferably 2% agar. Solid growth media is generally prepared by adding the agar to the growth medium prior to heat sterilization. Alternatively, a solid growth medium may be prepared by adding molten agar to sterile growth media.

Yeast host cells transformed with DNA constructs comprising DNA sequences encoding hybrid G protein-coupled receptors may be used in a variety of methods for detecting the presence of ligand in a test substance. These assays will generally include the steps of (a) exposing a culture of yeast host cells transformed with a DNA construct capable of directing the expression of a biologically active hybrid G protein-coupled receptor, wherein the receptor is a mammalian G protein-coupled receptor having at least one domain other than the ligand-binding domain replaced with a corresponding domain of a yeast G protein-coupled receptor, and wherein the yeast host cells express the biologically active hybrid G protein-coupled receptor, to the test sample under suitable conditions to allow binding of ligand to the hybrid G protein-coupled receptor and (b) detecting a biological response of the host cell and therefrom determining the presence of the ligand, wherein measuring is a means of detecting.

Suitable conditions to allow binding of ligand to a receptor are physiological conditions wherein the pH is maintained between 6 and 8, and the temperature is between 20° C. and 40° C. Preferably the pH is maintained between pH 7.4 and 7.5 and the temperature is between 22° C. and 23° C. As used herein, the binding of ligand to a receptor is understood to denote an interaction of a molecule with the ligand-binding domain of a receptor, which may result in a conformational change in the topology of the receptor. The binding of ligand to a receptor may either trigger or block a detectable biological response. Suitable biological responses for use in the present invention include the ability to mate, production of agglutinins, and adenylate cyclase activation. A particularly preferred biological response is cell division arrest in the G1 phase of cell division.

In one embodiment, the method comprises a culture of yeast cells transformed with a DNA construct capable directing the expression of a hybrid G protein-coupled receptor, wherein the receptor comprises a mammalian G protein-coupled receptor having at least one domain other than the ligand-binding domain replaced with a corresponding domain of a yeast G protein-coupled receptor, is suspended in an agar overlay on top an appropriate solid growth medium. The agar overlay is preferably between 0.6% and 2.5% agar, preferably 0.7% agar. The agar may or may not be diluted in an appropriate solid growth medium. A solution containing the test substance is added to wells in the assay plate. Alternatively, filters saturated with the test substance are laid on the surface of the agar overlay. The test substance diffuses through the agar overlay and binds to the hybrid G protein-coupled receptors, inducing a biological response. A halo of responding cells indicates that the test substance contains an agonist.

Antagonists are detected by their ability to reverse or prevent the G1 arrest of cells that have been treated with a known agonist. In one the method, a culture host cells transformed with a DNA construct capable of directing the expression of a hybrid G protein-coupled receptor, the receptor comprising a mammalian G protein-coupled receptor having at least one domain other than the ligand-binding domain replaced with a corresponding domain of a yeast G protein-coupled receptor, and wherein the yeast host cells express the hybrid G protein-coupled receptor, is suspended with an agonist in an agar overlay on top of an appropriate solid growth medium. The agonist induces a biological response of the host cells. A test substance is placed into wells in the assay plate or is saturated onto a filter that is laid on top of the agar. The test substance is allowed to diffuse through the media and competes with the agonist for binding to the hybrid G protein-coupled receptor. A halo of cells that have a reduced biological response colonies that the test substance contains an antagonist. In an alternate method, a culture yeast host cells transformed with a DNA construct capable of directing the expression of a hybrid G protein-coupled receptor, wherein the receptor comprises a mammalian G protein-coupled receptor having at least one domain other than the ligand-binding domain replaced with a corresponding domain of a yeast G protein-coupled receptor, and wherein the yeast host cells express the hybrid G protein-coupled receptor, are suspended in an agar overlay of on top of an appropriate solid growth media. A test substance is mixed with an agonist and is placed into wells in the assay plate or is saturated onto a filter that is laid on top of the agar overlay. The test substance diffuses through the media and the test substance competes with the agonist for binding to the hybrid G protein-coupled receptors. A halo of cells exhibiting a reduced biological response relative to the biological response of host cells exposed to the agonist alone indicates that the test substance contains an antagonist.

Within preferred embodiment, the presence of a ligand in a test substance is detected on the basis of the ability of agonists to induce the yeast mating response pathway or antagonists to compete with agonists for binding with the receptor. In a particularly preferred embodiment the method comprises *Saccharomyces cerevisiae* host cells transformed with a DNA construct capable of directing the expression of a biologically active hybrid G protein-coupled receptor, wherein the receptor comprising a mammalian G protein-coupled receptor having at least one domain other than the the ligand-binding domain replaced with a corresponding domain of a yeast G protein-coupled receptor, and wherein the yeast host cells express the biologically active hybrid G protein-coupled receptor, is also transformed with a second DNA construct comprising a mating-type specific promoter operatively linked to an indicator DNA sequence. Within this method, the host cells are exposed to a test ligand under suitable conditions to allow binding of ligand to the hybrid G protein-coupled receptors, and binding of ligand to the receptors is detected by detecting the expression of the indicator DNA sequence. Mating-type specific gene promoters include promoters of the *Saccharomyces cerevisiae* BAR1 gene, the *Saccharomyces cerevisiae* MFα1 gene, the *Saccharomyces cerevisiae* MFa1 gene, the *Saccharomyces cerevisiae* STE3 gene, the *Saccharomyces cerevisiae* STE2 gene, the *Saccharomyces kluveyri* gene, the *Saccharomyces cerevisiae* AGα1 gene, the *Saccharomyces cerevisiae* SST2 gene and the *Saccharomyces cerevisiae* FUS1 gene. A particularly preferred mating-type specific promoter for use in the present invention is the BAR1 promoter. Indicator DNA sequences include those DNA sequences whose expression results in a detectable biological response by the host cells. Suitable indicator DNA sequences include DNA sequences encoding nutritional markers that complement an auxotrophic host cell, DNA sequences that encode antibiotic resistance, and DNA sequences encoding enzymes capable of cleaving chromogenic substrates. A particularly preferred DNA sequence is the *E. coli* lacZ gene.

In a particularly preferred embodiment, the BAR1 promoter is operatively linked to the *E. coli* lacZ gene. The DNA construct is preferably integrated at the BAR1 locus in the yeast genome, resulting in a substitution of the DNA construct for some or all of the endogenous BAR1 coding sequence.

In a particularly preferred embodiment of the invention, a method for detecting the presence of ligand in a test substance utilizes a culture of *Saccharomyces cerevisiae* mating-type a haploid host cells transformed with a DNA construct capable of directing the expression of a hybrid G protein-coupled receptor, wherein the receptor comprises a mammalian G protein-coupled receptor having at least one domain other than the ligand-binding domain replaced with a corresponding domain of a STE2 gene product, and wherein the yeast host cells are transformed with a second DNA construct comprising the BAR1 promoter operatively linked to the *E. coli* lacZ coding sequence such that the second DNA construct is integrated at the BAR1 locus resulting in the substitution of into the host cell genome part or all of the BAR1 sequence. The method comprises the steps of (a) exposing the culture of transformed host cells to a test substance under suitable conditions to allow ligand to bind to the hybrid G protein-coupled receptor and detecting the induction of the BAR1 promoter by measuring the level of β-galactosidase produced. In one embodiment of the invention, β-galactosidase expression is detected by measuring the production of the yellow cleavage product o-nitrophenol resulting from the cleavage of the chromogenic substrate o-nitrophenyl-β-D-galactoside with the β-galactosidase in host cell lysates. In another embodiment the host cells may be suspended as a lawn in top agar and poured over a plate of the medium comprising an appropriate growth media that has been buffered between pH 6.8 and pH 7.0 and supplemented with X-gal. The medium may be buffered with A solution containing the test substance is added to the wells in the assay plate, or test substance-saturated filters are laid on the surface of the agar overlay. The test substance diffuses through the soft agar overlay and binds to the hybrid G protein-coupled receptors, causing an induction of β-galactosidase expression. Ligand binding is detected by identifying the halos of blue cells, which result from the production of the deep blue dibromodichloroindigo produced from the cleavage of X-gal by the β-galactosidase. Blue colonies indicate that the test substance is an effective agonist.

The following examples are offered by way of illustration and not by limitation.

EXPERIMENTAL

EXAMPLE 1

Cloning of the *Saccharomyces cerevisiae* STE2 gene

Figure 2:
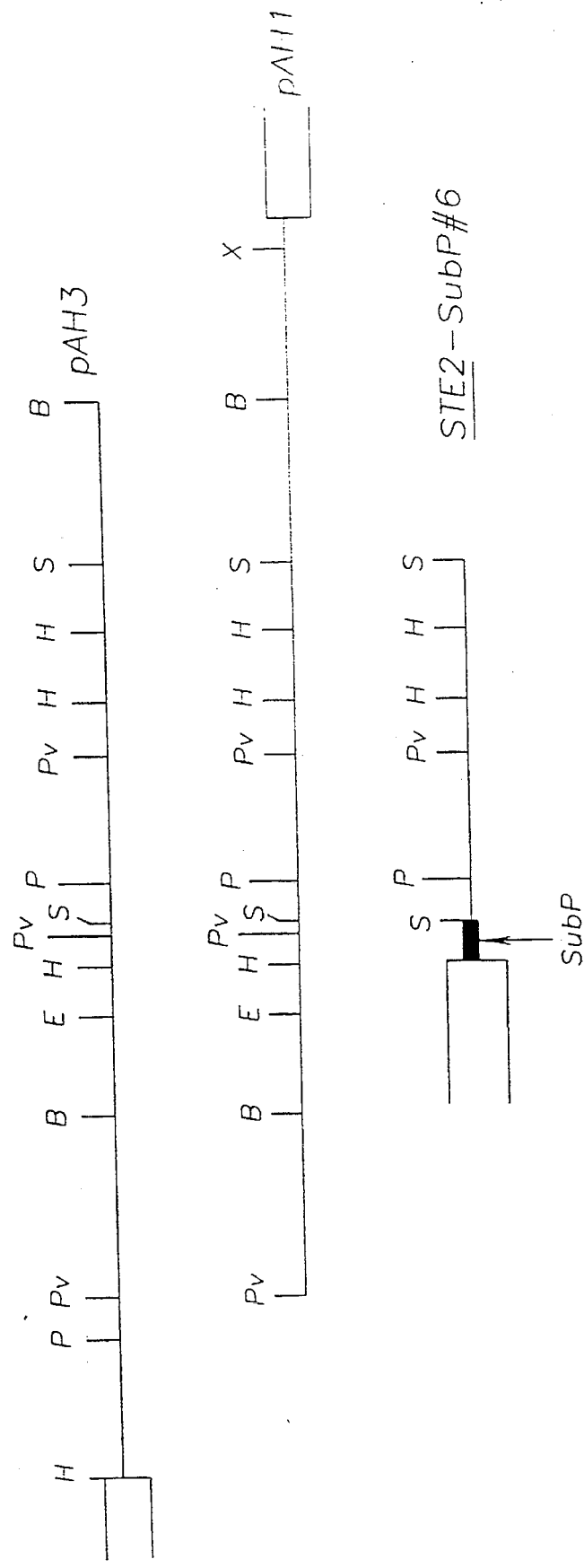
FIG. 2 illustrates a partial restriction map of representative STE2 clones pAH1, pAH2, pAH3 and STE2-SubP #6.

The STE2 gene was obtained as described by Hartig (*Mol. Cell Biol.* 6:2106–2114, 1986). Briefly, a DNA library containing total yeast genomic fragments in the vector YEp13, prepared as described by Nasmyth and Tatchell (*Cell* 19:753–764, 1980), was transformed into two leu2 yeast strains, each of which contained a ste2 mutation and was unable to mate. Transformed cells were isolated by selection on synthetic complete media lacking leucine. The Leu⁺colonies were screened for the ability to mate. Six colonies were identified that had acquired the ability to mate. Of the six colonies, five were found to contain different plasmids capable of complementing the ste2 mutations. The common region, found to be 2.6 kb in length, was demonstrated in plasmids pAH1 and pAH3 (FIG. 2). The 2.6 kb Pst I-Bam HI fragment from pAH1 was subcloned into the yeast vector pZUC12 (obtained from Mogens Hansen, Novo-Nordisk A/S, Bagsvaerd, Denmark), which comprises the *Saccharomyces cerevisiae* LEU2 gene and the origin of replication from the *Saccharomyces cerevisiae*2 µm plasmid in the *E. coli* plasmid pUC12. *Saccharomyces cerevisiae* ste2 host cells transformed with ethe resultant plasmid were found to be capable of mating, confirming that the 2.6 kb insert from pAH1 contained the STE2 structural gene. The identity of the cloned gene was further confirmed by integration into the host genome and subsequence Southern hybridization. The approximately 2 kb fragment of plasmid pAH1 was subsequently sequenced and was found to contain the 1.2 kb STE2 coding region and associated 5' flanking sequence. The DNA sequence of STE2 is shown in FIGS. 9A, 9B, 9C, and 9D.

The STE2 coding sequence present in pAH1 was subcloned into plasmid subPdimer-mp8 (Munro and Pelham, *EMBO J.* 3:3087–3093), which had been linearized with Sal I, to create plasmid STE2-SubP #6 (FIG. 2). This truncated STE2-substance P fusion, upon subcloning into the yeast vector YEp13 and transformation into ste2 mutant, was shown to encode a protein which is capable of complementing the Ste2 mutation in the host cell, allowing the cells to respond to α-factor and mate with MATa cells.

EXAMPLE 2

Expression of a Hamster β₂-Adrenergic Receptor-STE2 Fusions in Yeast Cells

A. Construction of DNA Constructs Encoding Hamster β₂-adrenergic receptor-STE2 Receptor Fusions A hamster β₂AR (Dixon et al. ibid., 1986) and the *Saccharomyces cerevisiae* STE2 gene product have been predicted to share the structure shown in FIG. 1. To study the relationship of the domains L2, L4 and L6 to ligand binding, the L2 and/or L4 domains of the STE2 gene product were replaced with the corresponding domains of the hamster β₂AR using in vitro mutagenesis (Zoller and Smith *DNA* 3:479–488, 1984) and linker addition.

The replacement of the STE2 L4 by the hamster β₂AR L4 was achieved by replacing the STE2 L4 with oligonucleotide adapters encoding the hamster β₂AR (FIGS. 3A, 3B, and 3C). Four oligonucleotides were designed to encode, upon annealing, a 5' Hha I adhesive end followed by nucleotides 554 to 573 of FIG. 8 encoding a portion of the STE2 TMD4 joined to a yeast codon-optimized hamster βAR L4 DNA sequence corresponding to nucleotides 522 to 585 of FIG. 3A followed by an Nsi I adhesive end. Referring to FIG. 4, plasmid pAH1 was cut with Sal I and Hha I to isolate the 1.3 kb fragment containing the partial coding region of STE2. Plasmid pAH1 was linearized with Sph I and partially cut with Nsi I to isolate the 0.8 kb fragment containing the STE2 sequences 3' to the STE2 L4. Oligonucleotides ZC1031 (Table 1), ZC1032 (Table 1), ZC1033 (Table 1), and ZC1034 (Table 1) were synthesized on an Applied Biosystems model 380A DNA synthesizer and purified by polyacrylamide gel electrophoresis. Olgonucleotides ZC1031 and ZC1032 were kinased. Adapters were formed by annealing oligonucleotide ZC1031 with oligonucleotide ZC1034 and by annealing oligonucleotide ZC1032 with oligonucleotide ZC1033 using the method essentially described by Maniatis et al. (ibid.) The vector pUC118 was linearized by digestion with Sal I and Sph I and ligated in a five part ligation with the two isolated fragments from pAH1 and the annealed pairs of oligonucleotides, ZC1031/ZC1034 and ZC1032/ZC 1033. The ligation mixture was transformed into *E. coli* strain JM83. Plasmid DNA prepared from the resultant transformants were isolated and sequenced to insure a correct fusion. A plasmid having the correct sequence comprising the STE2 gene having the STE2 L4 sequence replaced with a DNA sequence encoding a yeast codon-optimized hamster βAR1 L4 sequence was designated pHRS4 (FIG. 4).

TABLE 1

| | |
|---|---|
| ZC1031 | 5' CGC CTT TTG GTG AGT AGC AAC GAT CAT ACC CTT AAC AGC G3' |
| ZC1032 | 5' CTG TTA CCA CAA GGA AAC TTG TTG TGA CTT CTT CAC TAA TGC A 3' |
| ZC1033 | 5' TTA GTG AAG AAG TCA CAA CAA GTT TCC TTG TGG |

TABLE 1-continued

|  |  |
|---|---|
|  | TAA CAG TCG AT 3' |
| ZC1034 | 5' CTG TTA AGG GTA TGA TCG TTG CTA CTC ACC AAA AGG CGA TCG A 3' |
| ZC1039 | 5' ACT CTA TTT TAA ATA TCT CTT AAG TAA TTA CTC TTC AG 3' |
| ZC1040 | 5' TTA AGT GTT ATG AAG ATG TGG AAC TTC GGT AAC TTC TGG TGT GAA TTC TGG ACT TCT ATC GAC GG 3' |
| ZC1041 | 5' CGC CGT CGA TAG AAG TCC AGA ATT CAC ACC AGA AGT TAC CGA AGT TCC ACA TCT TCA TAA CAC 3' |
| ZC1042 | 5' ATG TTT ATG GCG CCA CAA ATA TAA T 3' |
| ZC1413 | 5' AAT TCT ACA C 3' |
| ZC1414 | 5' CAT GGT GTA G 3' |
| ZC2719 | 5' AAT TCA AAA AAT GTC TGA TGC GGC TCC TTC ATT GAG CAA TCT ATT TTA TGA TCC AAC GTA TAA TCC TGG TCA AAG CAC CAT TAA CTA CAC TTC CAT ATA TGG GAA TGG ATC CAC CAT CAC TTT CGA TGA GTT GCA AGG TTT AGT TAA CAG TAC TGT TGG CAT GGG CAT CGT CAT GTC TCT CAT CGT CCT GG 3' |
| ZC2720 | 5' CCA GGA CGA TGA GAG ACA TGA CGA TGC CCA TGC CAA CAG TAC TGT TAA CTA AAC CTT GCA ACT CAT CGA AAG TGA TGG TGG ATC CAT TCC CAT ATA TGG AAG TGT AGT TAA TGG TGC TTT GAC CAG GAT TAT ACG TTG GAT CAT AAA ATA GAT TGC TCA ATG AAG GAG CCG CAT CAG ACA TTT TTT G 3' |
| ZC2750 | 5' AAC ATT GTG CAT GTG ATC CAG GAT AAC CTC ATC CGT AAG GAA GTT TAC ATC CTC CTA AAT TGG ATA GGC TAT GTC AAT TCT GGT TTC AAT CCC CTT ATC TAC TGC CGG GCT GCT AAT AAT GCA 3' |
| ZC2751 | 5' TTA TTA GCA GCC CGG CAG TAG ATA AGG GGA TTG AAA CCA GAA TTG ACA TAG CCT ATC CAA TTT AGG AGG ATG TAA ACT TCC TTA CGG ATG AGG TTA TCC TGG ATC ACA TGC ACA TTG TT 3' |

The sequence encoding the STE2-$\beta_2$AR hybrid in plasmid pHRS4 was subcloned into the yeast shuttle vector YEp13 for expression in yeast. Plasmid pHRS4 was digested with Bam HI and Sph I to isolate the 2.3 kb fragment containing the STE2-$\beta$Ar fusion. Plasmid YEp13 was digested with Bam HI and Sph I to linearize the vector. The linearized vector was ligated with the STE2-$\beta$Ar fusion fragment. The resultant plasmid was designated pHRS6 (FIG. 4).

As shown in FIG. 5, the DNA sequence encoding the STE2 L2 was replaced with a DNA sequence encoding a yeast codon-optimized hamster $\beta$AR L2 after first inserting unique restriction sites on the borders of the STE2 L2 region. Oligonucleotides ZC1039 (Table 1) and ZC1042 (Table 1) were designed to place an Afl II site at the 5' border of L2 and a Nar I site at the 3' border of L2, respectively. Plasmid STE2-SubP #6 was subjected to in vitro mutagenesis using the method essentially described by Kunkel (*Proc. Natl. Acad. Sci. USA* 82:488–492, 1985). Oligonucleotides ZC1039 and ZC1042 were used as both first and second primers. After mutagenesis, mutants were selected and sequenced to identify plasmids containing both mutant sites. A correct plasmid containing an Afl II site and a Nar I site bordering the STE2 L2 was designated as STE2 #4 1039 +1042. The mutagenized STE2 coding sequence present in STE2 #4 1039+1042 was subcloned as a Eco RI-Bgl II fragment into Bam HI-Eco RI linearized pUC9 to generate plasmid pHRS7 (FIG. 5).

As shown in FIG. 5, the STE2 L2 was replaced by an oligonucleotide adapter containing the sequence for the hamster $\beta_2$AR L2 flanked by an Afl II site on the 5' end and a Nar I site on the 3' end. Oligonucleotides ZC1041 (Table 1) and ZC1040 (Table 1), which when annealed, encoded a yeast codon-optimized hamster $\beta_2$AR L2 adapter, corresponding to nucleotides 280 to 336 of FIG. 3A, were synthesized on an Applied Biosystems model 380A DNA synthesizer and purified by polyacrylamide gel electrophoresis. Oligonucleotides ZC1040 and ZC1041 were kinased and annealed using the method essentially described by Maniatis et al. (ibid.). Plasmid pHRS7 was digested with Eco RI and Nar I and with Eco RI and Afl II to isolate the approximately 0.85 kb STE2 fragment and the approximately 4.8 kb STE2+pUC9 fragment, respectively. The ZC1040/ZC1041 kinased adapter, the 0.85 kb Eco RI-Nar I STE2 fragment and the 4.8 kb STE2+pUC9 fragment were joined in a three-part ligation to generate pHRS8, which comprised a DNA sequence encoding STE2 having the STE2 L2 replaced with a yeast codon-optimized hamster $\beta_2$AR L2 (FIG. 5).

The mutant STE2 gene present in pHRS8 was subcloned into pJH50, a derivative of the yeast vector YEp13. YEp13 was modified to destroy the Sal I site near the LEU2 gene by partially digesting YEp13 with Sal I, followed by a complete digestion with Xho I. The 2.0 kb Xho I-Sal I fragment comprising the LEU2 gene and the 8.0 kb linear YEp13 vector fragment were isolated and ligated together. The ligation mixture was transformed into *E. coli* strain RR1. DNA was prepared from the transformants and was analyzed by digestion with Sal I and Xho I. A clone was isolated which showed a single Sal I site and an inactive Xho I site indicating that the LEU2 fragment had inserted in the opposite orientation relative to the parent plasmid YEp13. The plasmid was designated pJH50.

As shown in FIG. 5, plasmid pHRS8 was partially digested with Sal I and completely digested with Sma I to isolate the 2 kb mutant STE2 fragment. This fragment was ligated to pJH50 that had been linearized by digestion with Sal I and Pvu II. The resultant plasmid was designated pHRS5.

A yeast expression vector comprising a DNA construct encoding a STE2-hamster $\beta_2$AR fusion with the STE2 L2 and L4 replaced with the hamster $\beta_2$AR L2 and L4 was constructed as follows. Plasmid pHRS8 was digested with Sal I and Eco RV to isolate the 1.4 kb STE2-hamster $\beta_2$AR L2 fragment. Plasmid pHRS4 was digested with Eco RV and Hind III to isolate the 1 kb fragment comprising the STE2-hamster $\beta_2$AR L4 fragment. Plasmid pJH50 was linearized by digestion with Sal I and Hind III and was joined with the 1.4 kb Sal I-Eco RV fragment and the 1 kb Eco RV-Hind III fragment in a three-part ligation. The resulting plasmid was designated pHRS9 (FIG. 6).

B. Expression of STE2-Hamster $\beta_2$AR Fusions in Yeast

Plasmids pHRS5, comprising the DNA sequence encoding the STE2-hamster $\beta_2$AR L2 fusion; pHRS6, comprising the DNA sequence encoding the STE -hamster $\beta_2$AR L4 fusion; and pHRS9, comprising the DNA sequence encoding the STE2-hamster B$\beta_2$AR L2 +L4 fusion, were transformed into strains XH6-10B (MATa ste2-2 adeX leu2-2, 112 lys1 can1) and XH9-5C4 (MATa ste2-1 ade2-1 his3 leu2-2, 112 can1) using the method essentially described by Beggs (ibid.). Transformants were selected for their ability to grow on synthetic complete media lacking leucine.

EXAMPLE 3

Cloning of a Human $\beta_2$-Adrenergic Receptor cDNA

The human $\beta_2$AR cDNA was obtained from Brian K. Kobilka (Duke University Medical Center, Durham, N.C.; *Proc. Natl. Acad. Sci. USA* 84:46–50, 1987) as a 2.3 kb Eco RI fragment in the vector pSP65 (FIG. 8). Briefly, the human $\beta$AR cDNA was isolated from a human placental cDNA library cloned into the phage $\lambda$gt11. The library was screened using a $^{32}$P-labeled 1.3 kb Hind III fragment from the hamster $\beta_2$AR genomic clone. Five million recombinants were screened, resulting in the identification of five unique clones with inserts of 1.25 to 2 kb. Restriction enzyme analysis and cross hybridization demonstrated that the smaller clones represented fragments of the larger 2 kb clone. The 2 kb clone was sequenced using the dideoxy chain termination method. The DNA sequence and deduced amino acid sequence for human $\beta_2$AR are shown in FIG. 7A, 7B, 7C, and 7D.

EXAMPLE 4

Expression of a Human $\beta_2$-Adrenergic Receptor in Yeast Cells

The DNA sequence encoding a human $\beta_2$AR cDNA obtained from Kobilka (ibid.) was subcloned into a yeast expression vector for expression in yeast as follows.

The TPI1 promoter were obtained from plasmid pTPIC10 (Alber and Kawasaki, *J. Mol. Appl. Genet.* 1:410–434, 1982) and plasmid pFATPOT (Kawasaki and Bell, EP 171, 142; ATCC 20699). Plasmid pTPIC10 was cut at the unique Kpn I site, the TPI1 coding region was removed with Bal-31 exonuclease, and an Eco RI linker (sequence: GGA ATT CC) was added to the 3' end of the promoter. Digestion with Bgl II and Eco RI yielded a TPI1 promoter fragment having Bgl II and Eco RI sticky ends. This fragment was then joined to plasmid YRp7' (Stinchcomb et al., *Nature* 82:39–43, 1979) that had been cut with Bgl II and Eco RI (partial). The resulting plasmid, TE32, was cleaved with Eco RI (partial) and Bam HI to remove a portion of the tetracycline resistance gene. The linearized plasmid was then recircularized by the addition of an Eco RI-Bam HI linker to produce plasmid TEA32. Plasmid TEA32 was digested with Bgl II and Eco RI, and the 900 bp partial TPI1 promoter fragment was gel-purified. Plasmid pIC19H (Marsh et al., *Gene* 32:481–486, 1984) was cut with Bgl II and Eco RI and the vector fragment was gel purified. The TPI1 promoter fragment was then ligated to the linearized pIC19H and the mixture was used to transform *E. Coli* RR1. Plasmid DNA was prepared and screened for the presence of a ~900 bp Bgl II-Eco RI fragment. A correct plasmid was selected and designated pICTPIP.

Plasmid pMVR1 was then assembled. Plasmid pIC7 (Marsh et al., ibid.) was digested with Eco RI, the fragment ends were blunted with DNA polymerase I (Klenow fragment), and the linear DNA was recircularized using T4 DNA ligase. The resulting plasmid was used to transform *E. coli* RR1. Plasmid DNA was prepared from the transformants and was screened for the loss of the Eco RI site. A plasmid having the correct restriction pattern was designated pIC7RI*. Plasmid pIC7RI* was digested with Hind III and Nar I, and the 2500 bp fragment was gel-purified. The partial TPI1 promoter fragment (ca. 900 bp) was removed from pICTPIP using Nar I and Sph I and was gel-purified. The remainder of the TPI1 promoter was obtained from plasmid pFATPOT by digesting the plasmid with Sph I and Hind III, and a 1750 bp fragment, which included a portion of the TPI1 promoter, was gel purified. The pIC7RI* fragment, the partial TPI1 promoter fragment from pICTPIP, and the fragment from pFATPOT were then combined in a triple ligation to produce pMVR1 (FIG. 8).

As shown in FIG. 8, a plasmid comprising the $\beta_2$AR cDNA sequence in pSP65 was digested with Nco I and Sal I to isolate the 1.7 kb $\beta_2$AR fragment. Plasmid pMVR1 was digested with Eco RI and Sal I to isolate the approximately 3.7 kb fragment comprising the TPI1 promoter, the TPI1 terminator and pIC7RI* vector sequences. Synthetic oligonucleotides ZC1413 (Table 1) and ZC1414 (Table 1) were kinased and annealed (using methods essentially described by Maniatis et al. (ibid.)) to form an adapter having a 5' Eco RI adhesive end and a 3' Nco I adhesive end. The $\beta_2$AR fragment, the pMVR1 fragment and the synthetic adapters were joined by ligation. A plasmid comprising the TPI1 promoter, $\beta_2$AR cDNA, TPI1 terminator and pIC7RI* vector sequences was designated pHRS10 (FIG. 8).

The $\beta_2$AR expression unit of pHRS10 was subcloned into a derivative of the yeast vector YEp13, termed pJH50, for subsequent transformation into yeast. Plasmid pHRS10 was digested with Xho I and Hind III to isolate the approximately 2.6 kb expression unit comprising the TPI1 promoter, the $\beta_2$AR cDNA and the TPI1 terminator. Plasmid pJH50 was digested with Sal I and Hind III to isolate the 11 kb vector fragment. The 2.6 kb pHRS10 fragment and the 11 kb pJH50 fragment were joined in a two part ligation to generate plasmid pHRS11 (FIG. 8).

Plasmid pHRS11 was transformed into the *Saccharomyces cerevisiae* strains XP635-101ac-c1 (MATa leu2-3, 112 Aste2 Abar1::BAR1prom-lacZ gal1), ZY100 (MATa leu2-3, 112 ade2-10 suc2-Δ9 gal2 pep4::TPI1prom-CAT) and ZY400 (MATa leu2-3,112 ade2-101 suc2-Δ9 gal2 pep4::TPI1prom-CAT Amnn9::URA3) using the method generally described by Beggs (ibid.). Transformants were selected for their ability to grow in synthetic complete media lacking the amino acid leucine.

Transformants were assayed for the presence of biologically active $\beta_2$AR by radio-ligand binding using an assay adapted from the method described by Dixon et al. (ibid., 1987). The assay relies upon the displacement of labeled iodocyanopindolol ($^{125}$I-CYP), which binds nonspecifically to cell membranes in addition to $\beta_2$ARs and is considered a $\beta_2$AR antagonist, from the yeast-expressed $\beta_2$AR receptors by a $\beta_2$AR ligand. Plasmid pHRS11 transformants were inoculated into 250 ml of -LEUD medium (Table 2) and grown overnight at 30° C. The overnight cultures were diluted 1:2 into fresh -LEUD medium and were grown for two hours at 30° C. The log phase cells were pelleted by centrifugation, and the cells were washed in 20 ml of Binding Buffer (Table 2). The $A_{660}$ was taken of a 1:100 dilution to estimate the density of the cells.

TABLE 2

Media Recipes

—Leu ThrTrp Amino Acid Mixture 4 g adenine
3 g L-arginine
5 g L-aspartic acid
2 g L-histidine free base
6 g L-isoleucine
4 g L-lysine-mono hydrochloride
2 g L-methionine
6 g L-phenylalanine
5 g L-serine
5 g L-tyrosine
4 g uracil
6 g L-valine Mix all the ingredients and grind with a mortar and pestle until the mixture is finely ground.

-LEUD 20 g glucose 6.7 g Yeast Nitrogen Base without amino acids (DIFCO Laboratories Detroit, Mich.)

0.6 g -LauThrTrp Amino Acid Mixture

Mix all the ingredients in distilled water. Add distilled water to a final volume of 1 liter. Autoclave 15 minutes. After autoclaving add 150 mg L-threonine and 40 mg L-tryptophan.

Binding Buffer 15 mM Tris, pH 7.5

12.5 mM $MgCl_2$ 0.3 M EDTA

To measure receptor-bound ligand, the displacement of receptor-bound $^{125}$I-CYP was measured by subtracting the $^{125}$I-CYP counts bound in the presence of a known $\beta_2$AR ligand, such as alprenolol (ALP), from the counts of nonspecifically bound $^{125}$I-CYP. Competition binding experiments using $\beta_2$AR agonists and antagonists were measured by subtracting the $^{125}$I-CYP counts bound in the presence of serially diluted agonist or antagonist from the $^{125}$I-CYP counts bound in the presence of a saturating concentration of ALP.

Saturation binding experiments were carried out as follows. Increasing concentrations of $^{125}$I-CYP (New England Nuclear) were incubated with Binding Buffer containing $3\times10^8$ cells in the presence or absence of 10 μM ALP (Sigma, St. Louis, Mo.). The mixtures were incubated at 22° C. for one half hour. During the incubation, the mixture was vortexed one time. One ml aliquots of the mixture were loaded onto glass fiber G/FC Whatman filters. Cells were washed with ten volumes of Binding Buffer by suction. Filters were then counted on a gamma counter. Bound counts indicated the amount of bound $^{125}$I-CYP. Receptor-bound counts, determined by the equation below, were plotted as a function of the log of the concentration. The concentration of ALP found to saturate the $\beta_2$ARs expressed by the pHRS11 transformants was found to be at least 10M. One hundred times the saturation concentration of ALP was subsequently used for competition binding experiments.

[$^{125}$I-CYP]−[ALP+$^{125}$I-CYP]=receptor-bound counts where

[$^{125}$I-CYP]=total bound counts and [ALP+$^{125}$I-CYP]= nonspecifically bound counts Competition binding assays with isoproterenol, epinephrine and norepinephrine were carried out on the transformants as described above, except that a control tube comprising a saturating concentration of alprenolol of 1 mM+75 pM CYP added to $3\times10^8$ cells in 3 ml of Binding Buffer was prepared to determine the total availability of G protein-coupled receptor present on the host cells. In addition, assay tubes containing serial dilutions of isoproterenol, epinephrine, and norepinephrine (Sigma Chemical Co., St Louis, Mo.) mixed with 75 pM $^{125}$I-CYP were prepared. The percent maximal for the ligands isoproterenol, epinephrine, and norepinephrine were plotted as a function of the negative log of the concentration of the ligand. The percent of maximal for each ligand was determined using the equation below.

([$^{125}$I-CYP+ligand]−[exALP+$^{125}$I-CYP])÷([$^{125}$I-CYP]− [exALP+$^{125}$I-CYP])×100=maximal where

[$^{125}$I-CYP]=total bound counts exALP=an excess concentration of ALP capable of competing with $^{125}$I-CYP for all available receptor

[exALP+$^{125}$I-CYP]=nonspecifically bound counts in the presence of excess ALP

[$^{125}$I-CYP+ligand]=nonspecifically bound counts in the presence of a concentration of ligand Representative competition binding curves for ligand binding assays using isoproterenol, epinephrine and norepinephrine and ZY100 cells transformed with pHRS11 are shown in FIGS. 10 and 11.

EXAMPLE 5

Construction and Expression of Human $\beta_2$-Adrenergic-STE2 Hybrid Receptors

A. Construction of pHRS17

A DNA construct comprising a DNA sequence encoding a human β-adrenergic-STE2 receptor hybrid receptor was constructed by replacing the DNA sequence encoding the extracellular amino-terminal domain of the human $\beta_2$AR with a DNA sequence encoding the extracellular amino-terminal domain of the STE2 gene product. Plasmid pHRS16 was constructed as follows.

Oligonucleotides ZC2719 and ZC2720 were designed to encode a 5' end by an Eco RI adhesive end followed by the extracellular amino-terminal domain of the STE2 gene product containing nucleotides 1 to 147 of FIG. 9A joined to nucleotides 103 to 136 of FIG. 7A. Oligonucleotides were synthesized and phosphorylated on an Applied Biosystems model 380A DNA synthesizer and purified by polyacrylamide gel electrophoresis. The kinased oligonucletides are annealed using the method essentially described by Maniatis et al. (ibid.).

The plasmid comprising the $\beta_2$AR cDNA sequence in pSP65 is digested with Bal I and Sal I to isolate the 1.8 kb fragment comprising the $\beta_2$AR coding sequence from nucleotide 137 to 1242 of FIGS. 7A, 7B, 7C, and 7D. Plasmid pMVR1 is digested with Eco RI and Sal I to isolate the 3.7 kb fragment comprising the TPI1 promoter, TpI1 terminator and pIC7RI, vector sequences. The ZC2719/ZC2720 oligonucleotide adapter, the $\beta_2$AR fragment and the pMVR1 vector fragment are joined in a four-part ligation. The resultant plasmid was designated pHRS16.

The expression unit from pHRS16, comprising the TPI1 promoter, the STE2-$\beta_2$AR coding sequence and the TPI1 terminator, are subcloned into the yeast shuttle vector pJH50. Plasmid pHRS16 is digested with Hind III and Xho I to isolate the 2.8 kb expression unit. Plasmid pJH50 is digested with Sal I and Hind III to isolate the vector fragment. The pHRS16 and pJH50 fragments are joined by ligation, and the resulting plasmid is designated pHRS17.

B. Construction of pHRS18

A DNA construct comprising a DNA sequence encoding a hybrid human β₂AR-STE2 receptor is constructed from a human β₂AR coding sequence by replacing the DNA sequence encoding human β₂AR carboxy-terminal internal effector domain with the DNA sequence encoding the corresponding domain of the *Saccharomyces cerevisiae* STE2 gene product. Plasmid pHRS18 is constructed as follows.

Synthetic oligonucleotides were designed to encode a β₂AR-STE2 adapter comprising the nucleotide sequence of FIG. 6 from 877 to 985 joined the nucleotide sequence of FIG. 8 from 892 to 903 flanked by a 3' Nsi I adhesive end. The oligonucleotides were synthesized and phosphorylated on an Applied Biosystems model 380A DNA synthesizer and purified by acrylamide gel electrophoresis. The oligonucleotides are annealed using the method essentially described by Maniatis et al. (ibid.).

Plasmid pHRS10 is digested with Xho I and Hpa I to isolate the 1.7 kb fragment comprising the TPI1 promoter and 5' β₂AR cDNA sequences. Plasmid pAH3 is digested with Nsi I and Hind III to isolate the _kb fragment comprising the sequence encoding the 3' portion of the carboxy-terminal internal effector domain and the associated STE2 3' untranslated sequences. Plasmid pJH50 is digested with Sal I and Hind III to isolate the vector fragment. The ZC2750/ZC2751 adapter, the pHRS10 fragment, the STE2 fragment from pAH3 and the pJH50 vector fragment are joined in a four-part ligation. The resultant plasmid is designated pHRS18.

Although the foregoing invention has been described in some detail by way of illustration and example for purposes of clarity of understanding, it will be evident that certain changes and modifications may be practiced within the scope of the appended claims.

We claim:

1. A DNA molecule comprising a sequence encoding a biologically active hybrid G protein-coupled receptor, said receptor consisting of a mammalian G protein-coupled receptor having at least one domain other than a ligand-binding domain replaced with the corresponding domain of a yeast G protein-coupled receptor, wherein said domain is a third internal effector domain or a third internal effector domain and a carboxy-terminal internal effector domain.

2. The DNA molecule of claim 1 wherein the yeast G protein-coupled receptor is selected from the group consisting of the *Saccharomyces cerevisiae* STE2 gene product, the *Saccharomyces cerevisiae* STE3 gene product and the *Saccharomyces kluyveri* STE2 gene product.

3. The DNA molecule of claim 1 wherein the yeast G-protein-coupled receptor is the *Saccharomyces cerevisiae* STE2 gene product.

4. The DNA molecule of claim 1 wherein the mammalian G protein-coupled receptor is selected from the group consisting of β-adrenergic receptors, β-adrenergic receptors, muscarinic receptors, angiotensin receptors, substance K receptors and rhodopsin.

5. The DNA molecule of claim 1 wherein the mammalian G protein-coupled receptor is selected from the group consisting of human β₂-adrenergic receptors, human β₁-adrenergic receptors, human α-adrenergic receptors, human muscarinic receptors, human rhodopsin, human angiotensin receptors and human substance K receptors.

6. A DNA construct capable of directing the expression of a biologically active hybrid G protein-coupled receptor in a yeast cell, comprising the following operatively linked elements:

a transcriptional promoter;

a DNA molecule comprising a molecule encoding a biologically active hybrid G protein-coupled receptor, said receptor consisting of a mammalian G protein-coupled receptor having at least one domain other than a ligand-binding domain replaced with the corresponding domain of a yeast G protein-coupled receptor, wherein said domain is a third internal effector domain or a third internal effector domain and a carboxy-terminal internal effector domain, and a transcriptional terminator.

7. The DNA construct of claim 6 wherein the yeast G protein-coupled receptor is selected from the group consisting of the *Saccharomyces cerevisiae* STE2 gene product, the *Saccharomyces cerevisiae* STE3 gene product and the *Saccharomyces kluyveri* STE2 gene product.

8. The DNA construct of claim 6 wherein the yeast G-protein-coupled receptor is the *saccharomyces cerevisiae* STE2 gene product.

9. The DNA construct of claim 6 wherein the mammalian G protein-coupled receptor is selected from the group consisting of β-adrenergic receptors, α-adrenergic receptors, muscarinic receptors, angiotensin receptors, substance K receptors and rhodopsin.

10. The DNA construct of claim 6 wherein the mammalian G protein-coupled receptor is selected from the group consisting of human β₂-adrenergic receptors, human β₁-adrenergic receptors, human α-adrenergic receptors, human muscarinic receptors, human rhodopsin, human angiotensin receptors and human substance K receptors.

11. A yeast host cell transformed with a DNA construct capable of directing the expression of a biologically active hybrid G protein-coupled receptor, said receptor consisting of a mammalian G protein-coupled receptor having at least one domain other than a ligand-binding domain replaced with the corresponding domain of a yeast G protein-coupled receptor, wherein said domain is a third internal effector domain or a third internal effector domain and a carboxy-terminal internal effector domain.

12. The yeast host cell of claim 11 wherein the yeast host cell is a *Saccharomyces cerevisiae* cell.

13. The yeast host cell of claim 12 wherein the yeast host cell contains a genetically defective STE2 or STE3 gene.

14. The yeast host cell of claim 12 wherein the yeast host cell is a mating-type α haploid cell.

15. The yeast host cell of claim 12 wherein the yeast host cell is a mating-type a haploid cell.

16. The yeast host cell of claim 15 wherein the yeast host cell does not contain a functional BAR1 gene.

17. The yeast host cell of claim 15 wherein the yeast host cell is transformed with a second DNA construct comprising the BAR1 promoter operatively linked to the *E. coli* lacZ coding molecule, and the second DNA construct is integrated at the BAR1 locus.

18. A yeast host cell of claim 15 wherein the DNA construct comprises a DNA molecule comprising a sequence encoding a hybrid G protein-coupled receptor, wherein said receptor consisting of a mammalian G protein-coupled receptor having at least one domain other than a ligand-binding domain replaced with the corresponding domain of a yeast G protein-coupled receptor selected from the group consisting of the *Saccharomyces cerevisiae* STE2 gene product and the *Saccharomyces kluyveri* STE2 gene product, wherein said domain is third internal effector domain or a third internal effector domain and a carboxy-terminal internal effector domain.

* * * * *